(12) United States Patent
Longest et al.

(10) Patent No.: US 9,433,588 B2
(45) Date of Patent: *Sep. 6, 2016

(54) DELIVERY OF SUBMICROMETER AND NANOMETER AEROSOLS TO THE LUNGS USING HYGROSCOPIC EXCIPIENTS OR DUAL STREAM NASAL DELIVERY

(75) Inventors: Philip Worth Longest, Midlotian, VA (US); Michael Hindle, Glenn Allen, VA (US)

(73) Assignee: Virginia Commonwealth Univeristy, Richmond, VA (US)

( * ) Notice: Subject to any disclaimer, the term of this patent is extended or adjusted under 35 U.S.C. 154(b) by 705 days.

This patent is subject to a terminal disclaimer.

(21) Appl. No.: 13/503,927

(22) PCT Filed: Nov. 9, 2010

(86) PCT No.: PCT/US2010/055940
§ 371 (c)(1),
(2), (4) Date: Jun. 7, 2012

(87) PCT Pub. No.: WO2011/057235
PCT Pub. Date: May 12, 2011

(65) Prior Publication Data
US 2012/0251594 A1 Oct. 4, 2012

Related U.S. Application Data

(60) Provisional application No. 61/259,292, filed on Nov. 9, 2009, provisional application No. 61/306,105, filed on Feb. 19, 2010.

(51) Int. Cl.

| | |
|---|---|
| *A61K 31/137* | (2006.01) |
| *A61K 31/58* | (2006.01) |
| *A61K 31/5513* | (2006.01) |
| *A61K 31/7088* | (2006.01) |
| *A61K 38/02* | (2006.01) |
| *A61K 9/00* | (2006.01) |
| *A61K 9/12* | (2006.01) |
| *A61K 9/51* | (2006.01) |
| *A61M 16/06* | (2006.01) |
| *A61M 16/16* | (2006.01) |
| *A61M 16/10* | (2006.01) |
| *A61M 16/14* | (2006.01) |
| *A61M 15/08* | (2006.01) |
| *A61M 16/00* | (2006.01) |
| *A61M 16/08* | (2006.01) |
| *A61M 11/00* | (2006.01) |
| *A61M 15/00* | (2006.01) |
| *A61M 16/12* | (2006.01) |
| *A61M 16/20* | (2006.01) |

(52) U.S. Cl.
CPC ............ *A61K 31/137* (2013.01); *A61K 9/008* (2013.01); *A61K 9/12* (2013.01); *A61K 9/5115* (2013.01); *A61K 9/5123* (2013.01); *A61K 31/58* (2013.01); *A61M 11/001* (2014.02); *A61M 15/009* (2013.01); *A61M 15/08* (2013.01); *A61M 16/0057* (2013.01); *A61M 16/0666* (2013.01); *A61M 16/0875* (2013.01); *A61M 16/109* (2014.02); *A61M 16/147* (2014.02); *A61M 16/16* (2013.01); *A61M 11/00* (2013.01); *A61M 11/005* (2013.01); *A61M 15/00* (2013.01); *A61M 16/12* (2013.01); *A61M 16/20* (2013.01); *A61M 2202/0208* (2013.01); *A61M 2202/064* (2013.01)

(58) Field of Classification Search
CPC ............ A61K 9/0073; A61K 9/0075; A61K 9/0078; A61K 9/14; A61K 9/008; A61K 38/23; A61K 38/22
USPC ........... 424/489; 514/1.5, 1.6, 1.7, 9.7, 11.9, 514/21.3; 128/200.19, 200.23
See application file for complete search history.

(56) References Cited

U.S. PATENT DOCUMENTS

| | | |
|---|---|---|
| 5,874,063 A | 2/1999 | Briggner et al. |
| 7,186,401 B2 | 3/2007 | Keller et al. |
| 2003/0166509 A1* | 9/2003 | Edwards et al. ................. 514/3 |
| 2004/0171550 A1 | 9/2004 | Backstrom et al. |
| 2007/0140976 A1 | 6/2007 | Chen et al. |

FOREIGN PATENT DOCUMENTS

WO 2009/105445 A1 * 8/2009

OTHER PUBLICATIONS

Alshawa et al. (J. Phys. Chem. A., 2009, 119, 7678-7686).*
Persons et al.; "Maximization of pulmonary hygroscopic aerosol deposition"; Journal of Applied Physiology, vol. 63, No. 3, Sep. 1987; pp. 1205-1209.

(Continued)

*Primary Examiner* — Alma Pipic
(74) *Attorney, Agent, or Firm* — Whitham, Curtis & Cook, P.C.

(57) ABSTRACT

Pharmaceutically engineered aerosols (e.g. submicrometer and nano-particles and droplets) containing a hygroscopic growth excipient or agent are employed to improve the delivery of respiratory aerosols to the lung. Inclusion of the hygroscopic agent results in near zero depositional loss in the nose-mouth-throat regions and near 100% deposition of the aerosol in the lung. Targeting of the aerosol to specific lung depths is also possible. In addition, methods and apparatuses for delivering aerosols to the lung are provided. The aerosol is delivered to one nostril of a patient while a relatively high humidity gaseous carrier is delivered to the other nostril, resulting in post-nasopharyngeal growth of the aerosol to a size that promotes deposition in the lung.

11 Claims, 10 Drawing Sheets

(56) References Cited

OTHER PUBLICATIONS

Varghese et al.; "Particle deposition in human respiratory system: Deposition of concentrated hygroscopic aerosols"; Inhalation Toxicology, vol. 21, No. 7, Jun. 2009; pp. 619-630.

Peng et al.; "Study of the Hygroscopic Properties of Selected Pharmaceutical Aerosols Using Single Particle Levitation"; Pharmaceutical Research, vol. 17, No. 9, 2000; pp. 1104-1109.

Alshawa et al.; "Hygroscopic Growth and Deliquescence of NaCl Nanoparticles Coated with Surfactant AOT"; Journal of Physical Chemistry, vol. 113, No. 26, Jul. 2, 2009; pp. 7678-7686.

Martonen et al.; "Ambiant Sulfate Aerosol Deposition in Man: Modeling the Influence of Hygroscopicity"; Environmental Health Perspectives, vol. 63, 1985; pp. 11-24.

* cited by examiner

| Typical pharmaceutical aerosol (DPI 3 - 5 μm) | Nanoparticle delivery (100 – 1000 nm) | Nanoparticle Excipient Enhanced Growth - EEG) |
|---|---|---|
| ⇩ 3- 5 μm aerosol | ⇩ 100 – 1000 nm | ⇩ 100 – 1000 nm |
| Mouth-Throat<br>• 80% loss<br>• cleared or swallowed | Mouth-Throat<br>• <1% loss<br>• cleared or swallowed | Mouth-Throat<br>• <1% loss<br>• cleared or swallowed |
| ⇩ 3- 5 μm aerosol | ⇩ 100 – 1000 nm aerosol | ⇩ Hygroscopic growth to > 2μm |
| Lungs<br>• 10% TB<br>• 10% deep lung | Lungs<br>• 1% TB<br>• 30% deep lung | Lungs<br>• 10% TB<br>• 90% deep lung<br>• TB/deep lung distribution is controllable based on where size increase occurs |
| ⇩ ~ 1% exhaled | ⇩ ~ 70% exhaled (wasted) | ⇩ ~ 0% exhaled |

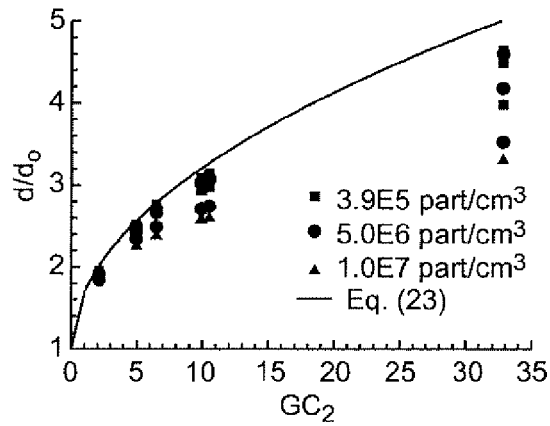
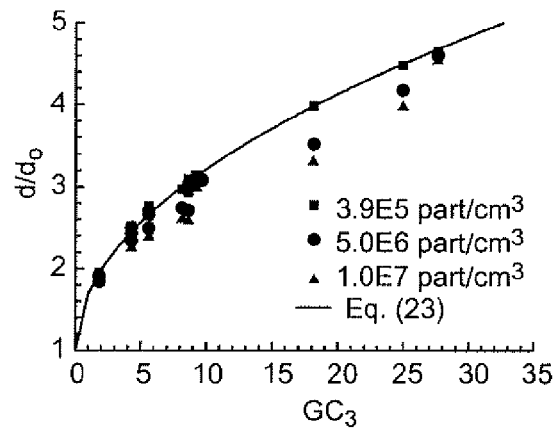
*Figure 10A*     *Figure 10B*
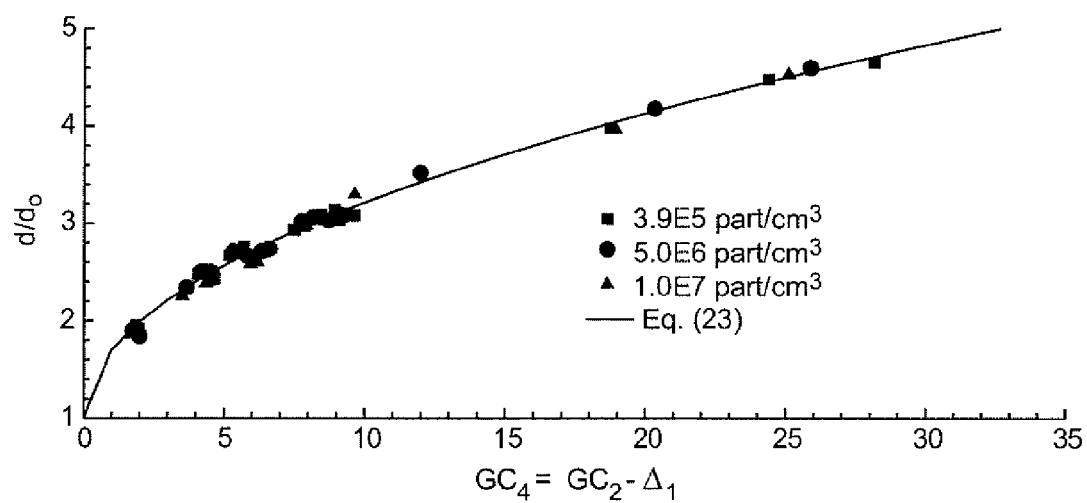
*Figure 10C*

DELIVERY OF SUBMICROMETER AND NANOMETER AEROSOLS TO THE LUNGS USING HYGROSCOPIC EXCIPIENTS OR DUAL STREAM NASAL DELIVERY

CROSS-REFERENCE TO RELATED APPLICATIONS

This application is a 371 of International Application PCT/US2010/055940 filed Nov. 9, 2010, which claims benefit to U.S Provisional Application 61/259,292 filed Nov. 9, 2009, and U.S. Provisional Application 61/306,105 filed Feb. 19, 2010, all of which are incorporated herein by reference.

BACKGROUND OF THE INVENTION

1. Field of the Invention

The invention generally relates to improved lung deposition of aerosols. In particular, in one embodiment, the invention provides aerosol formulations which are pharmaceutically engineered and formulated to contain hygroscopic excipients, and in another embodiment or a variation of the first embodiments, provides methods, apparatuses and systems for improved delivery of aerosols to the lungs using dual stream nasal delivery.

2. Background of the Invention

Nanoparticle aerosol drug delivery presents an advantageous route of administration for both locally and systemically acting pharmaceuticals. Inhaled nanoparticles in the size range of 40-1000 nm are capable of efficiently penetrating the mouth-throat (MT), nasal, and tracheobronchial (TB) regions of the lungs. Indeed, this nanoparticle size is optimum for transport into the peripheral lung regions, including the alveoli. However, once in the deep lung regions, the nanoparticles lack sufficient mass and inertia to deposit by sedimentation and impaction. Nanoparticles greater than approximately 40 nm also lack sufficient Brownian motion to deposit by diffusion. As a result, inhaled nanoparticles in the size range of 40-1000 nm often do not deposit in the lungs and are exhaled. Only a small fraction of inhaled nanoparticles actually deposit within the peripheral lung regions, with the majority, (about 70%) being exhaled (see FIG. 1).

The typical prior art solution to this problem is to deliver nanoparticles in conventional aerosol formulations, e.g. suspended in nebulized droplets, formulated as suspended particles in metered dose inhalers or combined with large carrier particles in a dry powder inhaler system. The primary limitations of these systems include the same drawbacks encountered by the current generation of inhaled pharmaceuticals. Namely, they are often deposited in the lung at very low deposition efficiencies. Perhaps as significant as the quantity of drug deposited is the large inter- and intra-subject variability that is often observed with these medicinal aerosols and the associated dose delivered to the lung. This is a particular problem for drugs with narrow therapeutic windows where accurate and reproducible dosing is essential. These commonly used inefficient aerosol drug delivery systems have particle sizes in the range of about 3-5 μm. For the delivery of 3-5 μm particles, deposition in the extrathoracic and upper TB airways may be significant (e.g. 80%, see FIG. 1). This deposition may be further enhanced by inhaler momentum effects, resulting in up to approximately 90% drug loss in the MT. Clearly, the present systems used for the delivery of pharmaceutical nanoparticles to the lungs are not optimal and result in poor drug delivery efficiency.

Non-invasive ventilation (NIV) is currently a form of standard care for patients suffering from respiratory insufficiency, sleep apnea, chronic obstructive pulmonary disease (COPD) and more severe acute and chronic respiratory failure. A common form of NIV is non-invasive positive pressure ventilation (NPPV) in which a mask or other interface supplies positive pressure flow to the nose and mouth. Extensive reviews have indicated the benefits of NPPV in adults and children. For less severe respiratory insufficiency and support, low-flow therapy (LFT) through a nasal cannula is common practice. In addition, high-flow therapy (HFT) has recently been introduced in which air or blended oxygen is preconditioned with heat and water vapor (humidity) to allow continuous delivery through a nasal cannula up to flow rates of 40 L/min. This approach is currently being applied to treat conditions such as pulmonary edema, COPD, bronchiectasis, and acute respiratory distress syndrome (post-intubation).

Patients receiving NIV typically have underlying respiratory and systemic conditions that can be effectively treated with a range of drugs administered non-invasively as pharmaceutical aerosols. However, both in vivo and in vitro studies have illustrated that high drug aerosol deposition losses occur in NIV tubing and delivery systems, resulting in very low delivery efficiencies on the order of <1-7% in both adults and children. Aerosol drug delivery to the lungs via NIV also employs conventional drug delivery devices (e.g. nebulizers and metered dose inhalers), that generate aerosols with relatively large particle sizes (3-5 μm). This large aerosol particle size results in high delivery system and nasal losses during NIV and may result in high variability in the amount of drug aerosol reaching the lungs. This is especially problematic for therapeutic substances with narrow therapeutic indices, and in fact, NIV may unfortunately not be appropriate for many next-generation medications, some of which have relatively narrow therapeutic windows. Moreover, high variability in delivery rates impacts the assessment of clinical trial results since the actual dose reaching a patient cannot be consistently established. However, despite low efficiency and associated problems, this current standard of care is often preferable to the alternative of temporarily halting NIV therapy for 10-30 minutes up to 2-8 times per day for administration of essential nebulized medications.

Clearly, improved methods for the pulmonary delivery of therapeutic agents are a desideratum in the medical field.

SUMMARY OF THE INVENTION

In one embodiment, denominated enhanced excipient growth (EEG), the present invention provides aerosolized submicrometer- or "nanometer"-sized drug particles and/or droplets which contain at least one hygroscopic excipient. The presence of the hygroscopic excipient facilitates particle/droplet growth during lung airway transit to a size that is generally not exhaled but rather is deposited in the lung. The hygroscopic excipient generally has a hygroscopic parameter of at least about 5 to about 80 or greater (in some embodiments, up to about 500, e.g. about 90, 100, 150, 200, 250, 300, 350, 400, or 450 or more), and usually at least 7 or greater. While prior art nanoparticles may exhibit some size increase upon exposure to the in vivo relative humidity of the lungs (~99.5%), the increase is insufficient to significantly increase lung retention. Therefore, a significant fraction of prior art drug particles are exhaled, and the medication is wasted. Incorporation of a hygroscopic excipient or agent in the appropriate proportions into the pharmaceutically engineered drug particles/droplets of the invention causes sufficient particle size growth to cause the particles/droplets to deposit in the lung. As a result, the initially small aerosol size results in significantly decreased extrathoracic (mouth-throat or nasal) deposition, and the subsequent aerosol size increase then results in improved lung delivery and allows for targeting the site of deposition. Therefore, less medication is wasted, more medication is delivered to an individual to whom the aerosol is administered, and the amount of medication that is delivered with each administration is more consistent, both for a single individual, and when comparing different individuals. In addition, the rate and extent of aerosol size growth can be controlled by the selection of the appropriate hygroscopic excipient (s) together with selection of the ratio of drug(s) and hygroscopic excipient(s) present in the particles or droplets.

In a second embodiment, denominated "dual stream nasal delivery", the present invention provides improved non-invasive ventilation (NIV) methods, apparatuses and systems for the lung delivery of aerosolized therapeutic agents using the nasal route. This embodiment involves delivering a first gaseous carrier (i.e. a gaseous transport medium or fluid) comprising an submicrometer aerosolized drug into one nostril of a patient while simultaneously delivering a second gaseous carrier into the other nostril, the second gaseous carrier generally having a higher water vapor content than the first gaseous carrier. When the two carrier streams meet in the nasopharynx area, moisture in the second stream mixes with the submicrometer aerosolized particles or is absorbed by submicrometer aerosolized droplets, causing them to increase in diameter and in weight as they travel through the airways and into the lungs. The increase in diameter and weight facilitates deposition in the lungs, and impedes exhalation of the particles or droplets. As a result, a much larger percentage of the aerosolized agent arrives at the intended destination (the lungs) and the amount of drug that is actually delivered to an individual in this manner is higher than occurs with previously known techniques. Further, the amount that is delivered between administrations to a single individual, or to different individuals, is more consistent than when prior art delivery methods are used. In addition, the rate and extent of aerosol particle size growth can be controlled by the water vapor content of the second air stream, to target deposition sites for the aerosol particles within the airways.

In some embodiments of the invention, EEG and the dual stream nasal delivery technology are combined, i.e. EEG particles/droplets may be delivered using dual stream nasal delivery technology.

BRIEF DESCRIPTION OF THE DRAWINGS

FIG. 1. Comparison of nanoparticle aerosol and standard (dry powder inhaler; DPI) delivery performance with the nanoparticle/droplet engineered for hygroscopic growth (EEG particle/droplet).

FIG. 3. Experimental system used to evaluate initial aerosol size and to determine aerosol growth over a short exposure period for comparisons with a numerical model.

FIG. 10A-C. Growth ratio over a range of multiple initial sizes (500-1500 nm) and aerosol number concentrations ($3.9 \times 10^5$-$1.0 \times 10^7$ part/cm$^3$) as a function of (A) $GC_2$ and (B) $GC_3$. As aerosol number concentration increases above $3.9 \times 10^5$ part/cm$^3$, use of both $GC_2$ and $GC_3$ produces an over prediction of growth due to two-way coupling. In contrast, $GC_4$ is shown (C) to account for growth across a wide range of drugs, excipients, initial sizes, and number concentrations.

DETAILED DESCRIPTION

Figure 2:
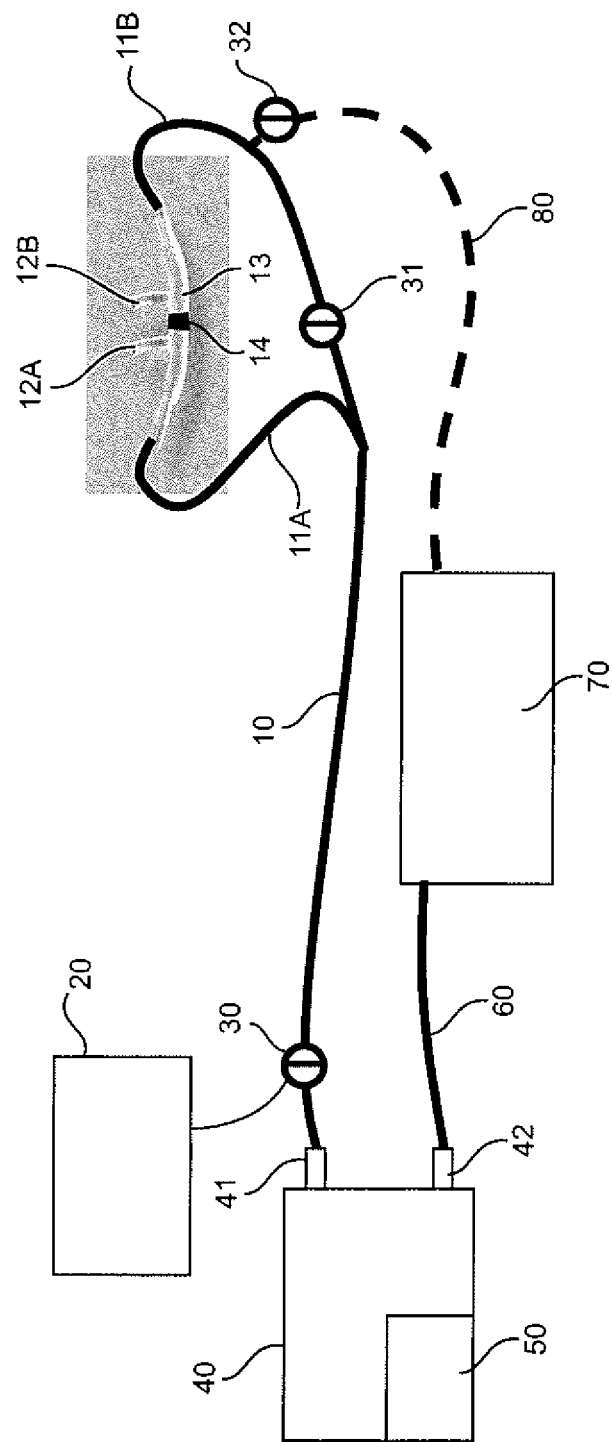
FIG. 2. Schematic representation of the dual stream nasal delivery system of the invention.

In a first embodiment, the invention provides novel compositions of aerosolized drugs (e.g. aerosolized droplets or particles) The nano- and submicrometer-sized particles or droplets of the invention are particularly suited to undergo hygroscopic growth because, contrary to prior art teachings, they contain, in addition to an active or therapeutic agent, at least one hygroscopic agent or excipent. The nano- and submicrometer particles or droplets are initially small enough to travel unimpeded through the MT region without significant deposition. However, after bypassing the MT region, the natural humidity in the lungs causes the particles or droplets containing the hygroscopic excipient(s) to accumulate water. Water accumulation increases the size and weight of the particles, and results in efficient penetration of the respiratory tract and near complete lung deposition. Exhalation of the aerosolized drug is thus avoided and consistent doses of high concentrations of inhaled drugs are delivered to aerosol recipients. The rate and extent of aerosol particle size growth can be controlled by selection of the appropriate hygroscopic excipient (s) together with selection of the ratio of drug and hygroscopic excipient present in the particle/droplet so as to target deposition sites for the aerosol particles within the airways. Nanoparticle EEG powders are provided for direct inhalation using appropriate dry powder inhalers. Suspension and solution EEG spray formulations are provided for incorporation in modified spray inhalers to produced submicrometer aerosols. Nebulizable suspensions and solutions for making these EEG particles/droplets are also provided, as are methods of treating a patient in need of respiratory therapy using the EEG aerosols. The suspensions and solutions comprise a fluid that is generally, but not always, a liquid (e.g. under pressure), until released from the container in which it is contained. As used herein, unless otherwise stated, the terms "particle" and "droplet" in the context of the invention generally refers to nanometer sized or sub-micron sized particles/droplets, i.e. those with an initial mass median aerodynamic diameter (MMAD) of less than about 1 micrometer.

In a second embodiment, the invention provides NIV methods, apparatuses and systems for aerosolized drug delivery. According to this "dual-stream" nasal delivery technology, a first heated and humidified gaseous carrier (e.g. air, $O_2$, mixtures of gases, etc.) is delivered to one nostril of a patient, and a submicrometer drug-containing aerosol is delivered to the other nostril in a second gaseous carrier that usually has a lower water vapor content than the first gaseous carrier. The gas or gases that make up the first gaseous carrier and the second gaseous carrier may be the same or different. The nasal septum separates the two carrier streams from each other during transit through the nasal passages, resulting in minimal aerosol size change and little deposition of the submicrometer aerosol particles/droplets as the aerosol passes through the NIV apparatus and nasal passages. Thereafter, the submicrometer drug aerosol and higher humidity carrier streams meet and mix in the nasopharynx region. Mixing of the two streams results in particle size growth of the aerosol particles/droplets by condensing or otherwise incorporating water from the higher relative humidity carrier stream, beginning in the nasopharynx region, and continuing as the particles or droplets travel downstream toward the lung. By the time the aerosol reaches the lung, drug particles/droplets have been formed which are large enough to favor deposition in lung tissue rather than exhalation. This approach is frequently carried out during or in conjunction with HFT via a nasal cannula that is modified to carry the dual gas streams. The rate and extent of aerosol particle size growth can be controlled by the water vapor content of the second gas stream in order to target deposition sites for the aerosol particles within the airways.

In some embodiments, these two embodiments of the invention are combined, i.e. EEG aerosols with hygroscopic excipients are delivered to a patient using dual-delivery stream technology. These two embodiments of the invention are described below.

I. Nanoparticles with Added Hygroscopic Excipient: Enhanced Excipient Growth (EEG)

One embodiment of the present invention, EEG, involves increasing the ability or tendency of a therapeutic substance in particulate or droplet form (e.g. nano- or submicrometer particles or droplets) to take on or accumulate water (and thus to increase its mass median aerodynamic diameter, MMAD) by adding to the substance a hygroscopic agent or excipient. According to the invention, the hygroscopic agent or excipient would generally not otherwise be associated with the therapeutic substance, or would be associated with the therapeutic substance in an amount that does not promote hygroscopic growth sufficient to result in efficient lung deposition of the substance when inhaled.

Hygroscopy is generally understood to be the ability of a substance to attract water molecules from the surrounding environment e.g. through absorption or adsorption. By "hygroscopic agent" or "hygroscopic excipient" (these terms are used interchangeably herein) we mean a substance that is able to attract water from the surrounding environment. In some embodiments, the hygroscopic agents are deliquescent materials (usually salts) that have a very strong affinity for moisture and will absorb relatively large amounts of water, forming a liquid solution. In the practice of the present invention, the hygroscopic growth of the nanoparticles that are administered is controlled by the hygroscopicity of the excipient and its percentage composition within the nanoparticle. In fact, by varying these parameters, it is possible to target deposition within specific lung regions by adjusting the amount of therapeutic agent and the amount and type of hygroscopic excipient in order to adjust the particle size growth potential of the particle/droplet. Particles/droplets formulated with a greater % of hygroscopic excipient or with a highly hygroscopic excipient are capable of taking on more water in the airways, and hence grow to a larger size and deposit higher in the airways (e.g. in the tracheobronchial region), than particles/droplets that are formulated to take on less water, which tend to deposit deeper in the airways (e.g. in the deep lung). As a result, nanosized aerosols can be effectively delivered past the MT or nasal regions and into the deep lung or to a specific tracheobronchial (TB) section.

In Example 3 below, a method to characterize the hygroscopic growth potential of excipient is described. A "hygroscopic parameter" is defined as $i_s \rho_s/M_s$ with units of kmol/m$^3$ where $i_s$ is the molecular dissociation constant, $\rho_s$ is the density, and $M_s$ is the molar mass of the solute. The subscript s indicates the solute, which may be a soluble drug or hygroscopic excipient. As shown in Example 4, the hygroscopic parameter collapses the data to a single curve indicating that it correlates well with the growth ratio. For combination particles, use of the hygroscopic parameter for both the drug and excipient to form a growth coefficient ($GC_2$) is also predictive of the aerosol particle size growth achieved. Use of the hygroscopic parameter was also found to be valid over a range of initial excipient-to-drug mass loading ratios. As a result, the hygroscopic parameter can be used to quantify the hygroscopic growth potential of both individual hygroscopic excipients and combination hygroscopic excipient-drug particles.

Values of the hygroscopic parameter for various drugs and excipients are provided in Table 3 of the Example 3. A model hygroscopic drug, albuterol sulfate, was observed to have a hygroscopic parameter of 4.9. Hygroscopic excipients to significantly enhance growth can then be defined as having a hygroscopic parameter approximately 50% greater than this model drug, or a hygroscopic parameter equal to or greater than about 7. In some embodiments, the hygroscopic parameter is equal to or greater than about 10. Therefore, materials that will serve as effective particle size growth excipients for the delivery of both hygroscopic and non-hygroscopic drugs in general will have a hygroscopic parameter of approximately 7 or greater. Based on the hygroscopic parameters provided in Table 3, all hygroscopic excipients considered satisfy the criterion of greater than about 7 and are therefore effective options for EEG delivery. This was also verified by the particle size growth predictions in Example 3. The envisioned range of hygroscopic parameters based on Table 6 is approximately 5 to 80; however, compounds with higher values are envisioned and encompassed by this invention. Also, hygroscopic parameters in a range of less than about 5 to greater than about 80 may be used to achieve particle size growth of non-soluble or non-hygroscopic drugs.

The underlying concept behind EEG is to provide an initial aerosol particle or droplet size small enough to avoid device/apparatus and extrathoracic (oral or nasal) depositional loss and then increase the size using hygroscopic excipients to result in full lung retention and, in some embodiments, to target the site of deposition in the lung. An initial small aerosol particle or droplet size (which includes both drug and hygroscopic excipient) is needed to reduce deposition in the aerosol generation device, delivery lines, patient interface, and extrathoracic airways. This is important for administering drugs to the lungs using the nasal route and also benefits the lung delivery of orally administered aerosols. On the other hand, the largest diameter possible is desirable to maximize drug payload while still providing negligible depositional drug loss. In addition, aerosol particle size also depends in part on the route of administration (oral or nasal), the inhalation flow rate, subject size and/or age (which affects airway dimensions), and disease state. Initial aerosol particles or droplets less than about 1 μm (1000 nm) in size will typically have very low depositional losses (e.g. particles with about 1000, 950, 900, 850, 800, 750, 700, 650, 600, or 550 nm MMAD). However, initial aerosol particles or droplets less than about 500 nm and even as small as about 200 nm (e.g. about 450, 400, 350, 300, or 250 nm) in size may be necessary for some applications, such as with long delivery lines (e.g. lines>about 5 cm in length), standard or thin delivery lines (e.g., lines with diameters of about 30, 10, or 5 mm, or less), nasal cannula applications (which inherently have relatively long delivery lines and thin nasal prongs with diameters of about 7, 5, 3 mm, or less), and delivery to infants or small laboratory animals. Particle or droplet sizes smaller than approximately 40 nm will generally not likely be employed because of increased depositional losses due to Brownian motion, i.e. the smallest sizes utilized will generally be in the range of from about 40, 45, 50, 55, 60, 65, 70, 75, 80, 85, 90, 95, 100, 125, 130, 135, 140, 145, 150, 155, 160, 165, 170, 175, 180, 185, 190, 195, and 200 nm MMADs. Larger sizes, say up to about 1.5 μm (e.g. about 1.1, 1.2, 1.3, or 1.4 μm) may also be considered to maximize drug payload for sufficiently low inhalation flow rates, or for short distances where deposition is targeted to the upper airways (e.g. nasal cavity or trachea).

Generally, the addition of a hygroscopic agent to a therapeutic substance forming an initially small aerosol particle or droplet as described herein and exposure to a humidified airstream or the humidified lung airways causes an increase in MMAD of an average particle or droplet of at least about 2 to about 200-fold, and usually at least from about 3 to about 5 fold (e.g. a 800 nm particle would increase in MMAD to at least about 2.4 μm (2400 nm), and possibly to about 4.0 μm (4000 nm) or even greater, than would occur without the hygroscopic excipient. Thus a particle may, as a result of the addition of a hygroscopic agent, increase in MMAD, after inhalation and during passage through the airways, by about 2, 3, 4, 5, 6, 7, 8, 9, or 10 fold, or even more.

This increase in MMAD increases the amount of the therapeutic substance that deposits in the lungs usually at least from about 2 to about 200-fold, and usually at least from about 3 to about 5 fold (e.g. lung deposition of a particle that, without added hygroscopic excipient, deposits at a rate of about 25% might increase to about 75% or even higher (up to e.g. from about 90, 95, or even close to 100%). The quantity of therapeutic agent that is deposited is thus generally increased by about 2, 5, 10, 20, 30, 40, 50, 60, 70, 80, 90 or 100 fold, or even more, depending on the therapeutic agent, and the amount and characteristics of the hygroscopic agent that is used. A corresponding decrease in the amount of drug that is exhaled also occurs.

Hygroscopic agents that may be used in the practice of the invention include but are not limited to: salts such as NaCl, KCl, zinc chloride, calcium chloride, magnesium chloride, potassium carbonate, potassium phosphate, carnallite, ferric ammonium citrate, magnesium sulfate, sodium sulfite, calcium oxide, ammonium sulfate; sugars such as sorbital, mannitol, glucose, maltose, galactose, fructose, sucrose; glycols such as polyethylene glycols (varying molecular weights), propylene glycol, glycerol; organic acids such as citric acid, sulfuric acid, malonic acid, adipic acid; lactams such as 2-pyrrolidone, polyvinylpolyprrolidone (PVP); other substances include potassium hydroxide, sodium hydroxide, gelatin, hydroxypropyl methylcellulose, pullalan, starch, polyvinyl alcohol, and sodium cromoglycate.

The amount of hygroscopic excipient that is formulated with the therapeutic substance, either as a dry powder particle or in a formulated drug solution from which aerosolized droplets are generated generally ranges from about 1% by weight to about 99% by weight, typically from about 2% to about 95% by weight, and more typically from about 5% to 85% by weight (i.e. % of the total particle weight). The amount varies depending on several factors. The amount varies, e.g. according to the type of therapeutic agent(s) (more than one therapeutic substance may be present in a particle/droplet) and/or other substances (and other substances such as buffering substances, bulking agents, wetting agents, etc., see below), that are present in the particle/droplet, as well as the particular hygroscopic excipient that is used. In addition, the ratio of drug and hygroscopic excipient present in the initial particle or droplet is determined by the rate and extent of aerosol particle size growth that is required to target deposition sites for the aerosol particles within the airways.

Figure 7A:
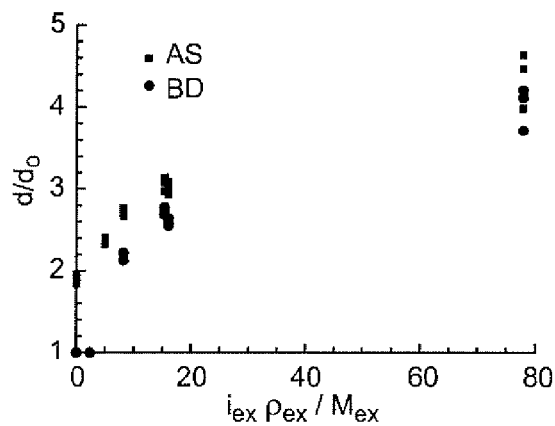
FIG. 7A-B. Diameter growth ratios for AS and BD combination particles with each hygroscopic excipient based on (A) the hygroscopic growth parameter and (B) $GC_2$, which accounts for the growth potential of both the excipient and drug. Use of the $GC_2$ parameter collapses the growth data to an approximate single curve for combination drug and excipient particles.
Figure 7B:
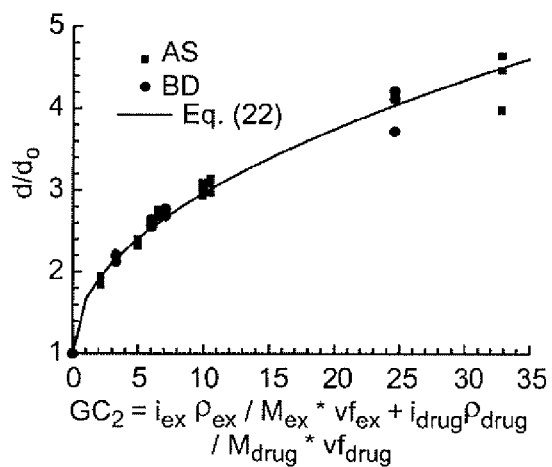

Example 3 shows how the hygroscopic parameter (defined above) of both the excipient and drug can be combined into a growth coefficient. This growth coefficient can then be used to predict the amount of expected size increase for a specific initial particle/droplet or it can be used to engineer initial particle/droplet properties to achieve a predetermined size increase to target deposition sites for the aerosol particles within the airways. Briefly, growth coefficient $GC_2$ in Example 3 is defined for combination drug—hygroscopic excipient particles/droplets as the hygroscopic parameter of each compound (i.e. for each drug and for each hygroscopic agent in the particle/droplet), times the initial soluble volume fraction of each compound summed for all soluble compounds (both drugs and excipients; see Eq. (21)). This can be applied to the initial particles, where the volume fraction of the solutes sum to 1, and the initial droplets, where the volume fractions of the solutes sum to less than 1. Eq. (22) can then be used to predict the amount of expected growth under respiratory inhalation conditions (e.g. 2 second (s) exposure in adult airways), which is illustrated in FIG. 7B. Specifically, a $GC_2$ of 2.8 is required to double the initial particle/droplet size under standard adult respiratory conditions. As shown in FIG. 7B, higher GC values result in larger size increases, and GC values greater than 2.8 may also be employed, e.g. GC values of at least about 3, 4, 5, 6, 7, 8, 9, 10, 15, 20, 25, 30 or 35 may be used.

The $GC_2$ parameter can also be used to engineer the initial particle or droplet properties to achieve a specific amount of growth. As an example, albuterol sulfate (AS) is to be delivered as a model drug in combination with NaCl as a model excipient to achieve a size increase from 900 nm to 3.5 µm, resulting in a final to initial diameter ratio of 3.89. Equation (22) predicts that the $GC_2$ value of an initially dry particle should be 23.2. The hygroscopic parameters of AS and NaCl are 4.9 and 77.9 (Table 6). The definition of the $GC_2$ parameter (Eq. (21)) can then be used to determine that the volume fractions of AS and NaCl in the initial 900 nm particle should be 0.75 and 0.25, respectively, in order to achieve an MMAD increase from 900 nm to 3.5 µm. Based on known relationships between volume and mass, these initial volume fractions translate to initial AS and NaCl mass fractions of 0.65 and 0.35, respectively. The predicted initial volume or mass fractions can then be used as the initial mass loadings for combination particle formation, for example using a spray drying process or for defining the ratio of drug and hygroscopic excipient in a solution formulation that will be subsequently aerosolized. Example 3 also demonstrates the use of modified growth "factors" to better account for the initial aerosol size and aerosol particle/droplet numbers (Equations 23-27 and FIGS. 9 & 10). The relationships presented here and in Example 3 can be applied to both the initial particles and droplets. For droplets, the initial volume fraction of water is not included in the calculation of the growth coefficient. For water insoluble drugs like budesonide, the soluble volume fraction term in the growth coefficient equation is set equal to zero. Replacing albuterol sulfate with budesonide in the example above, the drug and hygroscopic excipient volume fractions to achieve a diameter growth ratio of 3.89 are 0.70 and 0.30, respectively. For droplet delivery, albuterol sulfate and NaCl with an initial water volume fraction of 0.25 is considered. To achieve a size increase from 900 nm to 3.5 µm of this droplet, the initial volume fractions of AS and NaCl are 0.48 and 0.27, respectively.

The use of different excipients, in combination with the initial mass loading of whichever excipient is selected, can be used to achieve predetermined growth ratios (as shown above) and target deposition to specific regions of the respiratory tract. For targeted deposition, the desired aerosol size increase depends on the targeted deposition site (which may be, for example, the whole lung, the alveolar airways, the tracheobronchial (or conducting) airways, or a portion of the tracheobronchial region), the inhalation flow rate and waveform, and the inhalation time or volume inhaled. For typical respiratory parameters, growth to approximately 2.0 µm and above (e.g. to about 1.5, 2.0, 2.5, 3.0, 3.5, or 4.9 µm, or higher) can be used to provide good lung retention of the aerosol in adults. Larger or smaller final diameters may be needed to provide full lung retention in children and animals, which have different lung anatomies and breathing parameters. For example, growth to approximately 1.0 µm and above (e.g. to about 1.5, 2.5, 3.0, 3.5, 4.0 µm or higher) can be used to provide good lung retention of the aerosol in most children. Aerosol size for full lung retention in animals is species dependent, and can range from about 1 to about 10 µm and larger. Targeting deposition primarily to the tracheobronchial region generally requires growth to sizes greater than 2.0 µm (e.g. about 2.5, 3.0, 3.5, or 4.0 µm and above) under typical breathing conditions in adults. Targeting deposition to the upper tracheobronchial airways generally requires growth to 3 µm and above (e.g. about 3.5, 4.0, 4.5, or 5.0 µm, or greater). These targeting size values will change as a function of inhalation properties and subject anatomy factors such as age, disease state, and species (e.g. human, laboratory animal, etc.). Desired final aerosol sizes and rates of growth for achieving full lung retention or targeting deposition within specific regions can be determined using either existing numerical models or deposition correlations from in vivo experiments. Numerical models of respiratory deposition are particularly well suited to determine the desired final aerosol sizes for a variety of breathing parameters and subject anatomies. Computational fluid dynamics (CFD) modeling can be used to make highly accurate predictions of both aerosol growth and deposition in three-dimensional models of the airways under realistic breathing conditions, and thereby determine the desired initial particle properties for targeting deposition in specific lung regions.

The hygroscopic-loaded aerosols of the invention may be delivered by any of the many known methods of delivering aerosolized substances to patients. Drug—hygroscopic excipient particles may be pre-formed using the techniques described herein or formed during the aerosolization process, depending upon the aerosol delivery device. Three main classifications of delivery systems are commonly used: dry powder inhalers (e.g. active and passive dry powder inhaler or other methods of aerosolizing powders), spray systems (e.g. pressurized metered dose inhalers, soft mist inhalers, and other methods of forming sprays), and nebulizers (including jet and mesh and other methods of breaking up liquids). Examples of dry powder inhalers may include the currently available commercial inhalers such as Diskus® (GlaxoSmithKline), Turbuhaler® (AstraZeneca) or newly designed inhalers that are optimized for the delivery of sub-micrometer or nano-sized dry powders. For these devices, the particles would be manufactured to produce drug and hygroscopic excipient combination particles with a sub-micrometer/nanometer particle size. Techniques such as spray drying, using the Buchi nano spray dryer may also be employed. During spray drying, a solution which may be an aqueous solution, or a mixture of an organic solvent and water containing the drug and the hygroscopic excipient is atomized into a spray. Mixing occurs as the spray and air are combined followed by drying of the droplets to produce submicrometer sized particles at elevated temperature. The particles are collected and then loaded into the selected dry powder inhaler for administration to the patient. The final particle size is dependent upon the proportion of organic and aqueous solvent in the initial solution, the drug and hygroscopic excipient content and drying temperature. In a similar way, the capillary aerosol generator has been employed to produce drug-hygroscopic excipient particles. Other techniques for producing drug and hygroscopic particles include sonocrystallization, precipitation using supercritical fluids and other controlled precipitation techniques including in situ micronization, high gravity anti-solvent precipitation and solvent-anti-solvent crystallization, and coating of the drug particles with hygroscopic excipient. For spray inhaler delivery systems (e.g. metered dose inhalers, AERx™ (Aradigm, Hayward, Calif.)), Respimat® (Boehringer Ingelheim, Ingelheim, Germany), and the capillary aerosol generator (Philip Morris USA) together with other applicable spray generation mechanisms such as electrospray and electrohydrodynamic spray aerosols (Mystic, Ventaira), two formulation options are available. Firstly, pre-formed drug—hygroscopic excipient combination particles, produced using the methods described above, which are insoluble are suspended in a spray solvent (e.g. drug and hygroscopic pre-formed particle suspended in a hydrofluoroalkane or other propellant for a metered dose inhaler system, or suspended in water or other suitable solvent for a soft mist inhaler). Secondly, a solution formulation of soluble drug and hygroscopic excipient in the spray solvent (e.g. drug and hygroscopic excipient dissolved in a hydrofluoroalkane propellant or other propellant for a metered dose inhaler or dissolved in water or other suitable solvent for a soft mist inhaler). The addition of a co-solvent (e.g. ethanol) or mixtures of spray vehicles (e.g. HFA 134a and HFA 227 in varying proportions for an MDI formulation or water and glycerol in varying proportions for a soft mist inhaler) may be required to completely dissolve the drug and excipient. Combination drug—hygroscopic excipient particle or droplet formation in these spray systems is by a spray atomization mechanism. For these spray systems, a combination of the spray nozzle actuator size and the formulation composition that determines the size of the particles or droplets formed, has been described by Stein, S. W. and Myrdal, P. B. (2004) for metered dose inhalers. For the EEG particles, these spray conditions are optimized to produce submicrometer spray aerosols in contrast to the conventional 3-5 μm spray systems. The same two options are available for nebulizer formulations. Pre-formed drug—hygroscopic excipient combination particles, produced using the methods described above, which are insoluble are suspended in a nebulization vehicle. Or a solution formulation of soluble drug and hygroscopic excipient in the nebulization vehicle is employed depending upon the physico-chemical characteristics of the drugs and hygroscopic excipient. Liquid nebulizer spray systems employ either a jet nebulizer, an ultrasonic nebulizer, a pulsating membrane nebulizer, a nebulizer with a vibrating mesh or plate with multiple apertures, or a nebulizer comprising a vibration generator and an aqueous chamber. Examples of which include the LC Jet Plus (PARI Respiratory Equipment, Inc., Monterey, Calif.), T-Updraft II (Hudson Respiratory Care Incorporated, Temecula, Calif.), Pulmo-Neb (DeVilbiss Corp. Somerset, Pa.), Acorn-1 and Acorn-II (Vital Signs, Inc., Totowa, N.J.), Sidestream (Medic-Aid, Sussex, UK), MicroAir (Omron Healthcare, Inc., Vernon Hills, Ill.), and UltraNeb 99 (DeVilbiss Corp. Somerset, Pa.) may be used in the methodology of the invention. Handheld portable spray aerosol generators employ either a piezoelectric mechanism, electro-hydrodynamic and/or are based on the vibrating membrane with pores, examples of which include the eFlow® (PARI Respiratory Equipment, Inc., Monterey, Calif.), eFlow® Baby (PARI Respiratory Equipment, Inc., Monterey, Calif.), AeroNeb® (Aerogen, Inc., Mountain View, Calif.), Aero Dose™ (Aerogen, Inc., Mountain View, Calif.), Halolite™ (Profile Therapeutics Inc., Boston, Mass.), MicroAir® (Omron Healthcare, Inc., Vernon Hills, Ill.), TransNeb™ (Omron Healthcare, Inc., Vernon Hills, Ill.). Similarly, the nebulization conditions require optimization to produce submicrometer dry particle aerosols or droplets using appropriate drying techniques.

The aerosol may be delivered to ambulatory patients, in conjunction with mechanical ventilation systems, and in conjunction with non-invasive ventilation systems. In addition to improving the delivery of aerosols to ambulatory patients, EEG provides an effective method to improve aerosol delivery to patients receiving invasive and non-invasive mechanical ventilation. The initially small aerosol size can easily penetrate the delivery lines of mechanical ventilation systems, where depositional losses are often high. Submicrometer aerosol size will also reduce deposition in the patient interface (mask, cannula, or endotracheal tube) and upper airways. Subsequent growth in the patient's airways is then used to promote lung deposition of the aerosol. In this embodiment, delivery may be via a prior art cannula (e.g. by HFT or LFT), catheter, tracheal tube, face mask, by oral intubation, by NPPV, by a nasal tube, etc. The particles may be particularly useful when traditional LFT delivery is employed, as this delivery mode typically does not employ heated or moistened air. Alternatively, the aerosol may be delivered in a separate line with low water vapor content or the humidification of the ventilation system may be temporarily turned off. In some embodiments, the hygroscopic aerosols of the invention are delivered by means of the dual stream nasal delivery system described herein in section II.

The EEG aerosols of the invention may be used in any situation in which it is desired to deliver aerosolized particles or droplets to the lungs or targeted regions of the lungs. One envisioned application is for the effective delivery of aerosols to animals during pharmacological and toxicological testing of drugs, pollutants, etc. The complex nasal airways of most test animals result in high depositional losses and complicate the analysis of lung absorption and toxicity testing. EEG can be used to reduce nasal depositional losses in animals and deliver higher fractions of the drug, pollutant, etc. to the lungs. This improvement reduces uncertainties associated with animal to human extrapolations of results, which makes in vivo pulmonary testing in animals more realistic and effective.

Another particular application for EEG is infant or neonatal care. The nasal route of administration of therapeutic substances is required for infants, who usually always breathe through their nose. Currently, only ~1% of the drugs nasally administered to infants reach the lungs. The present technology improves infant and neonate lung delivery to approximately 90%, which results in less wasted drug, better clinical outcomes, and less frequent administration and hence fewer deleterious side effects.

Examples of agents that may be formulated with a hygroscopic excipient are presented in section III below.

II. Lung Aerosol Delivery Using Dual Stream Nasal Delivery

This embodiment of the invention is typically implemented in conjunction with the delivery of beneficial gaseous carrier substances, frequently oxygen, via a nasal cannula using, for example NIV technology such as HFT. Persons receiving oxygen therapy often are also in need of or can benefit from therapy with other medicaments which are preferably delivered directly to the lungs or which can optionally be delivered via the lungs as inhaled aerosols but which then are distributed systemically. In prior art NIV systems, the delivery of inhaled aerosols necessitates the cessation of NIV in order to administer the inhaled aerosol agent. This is inconvenient and, as described in the Background section, the delivery of therapeutic agents via prior art inhalers can be inefficient. The present invention eliminates both these concerns. According to the present invention, aerosolized therapeutic agents are delivered simultaneously with NIV therapy. Specifically, for HFT therapy, a "nano"- or submicrometer-sized drug aerosol is delivered to one nostril of a patient using a carrier gas (e.g. air, helox (oxygen—helium blends), or other suitable carrier gases) while concomitantly, a carrier gas with higher water vapor content is delivered to the other nostril. In other words, the amount of moisture (water vapor) in the second gaseous stream is generally higher than that of the first stream which carries the submicrometer aerosol. The nasal septum initially separates the two streams while they traverse the nasal cavity, and the aerosol is sized so that deposition in the nasal region is unlikely, as described elsewhere herein. Upon reaching the nasopharynx region, the two carrier streams meet and mix. Aerosol particles or droplets from the first gaseous stream encounter the elevated level of moisture in the second stream and undergo particle size growth by taking on water. Their resulting increase in size and weight increases their tendency to enter and deposit in the lungs, and decreases their tendency to be exhaled.

A schematic representation of one embodiment of a system or apparatus capable of delivering aerosolized agents in this manner is shown in FIG. 2. FIG. 2 shows a nasal cannula comprising flexible delivery tube (line) 10 with branches 11A and 11B, aligned by optional connector 13. Open ends 12A and 12B are fashioned so as to be directly insertable into the nostrils of a patient (e.g. 12A may be inserted into a left nostril and 12B into a right nostril. Connector 13 may or may not be present; in some embodiments, open ends 12 A and 12B are directly attached to branches 11A and 11B, respectively, without the intervening connector, although the connector serves to conveniently hold and position these components. If connector 13 is present, it is constructed so that the streams of gaseous carrier flowing through branches 11A and 11B and into and out of open ends 12A and 12B do not mix, i.e. divider or wall 14 is present within connector 13 to prevent mixing. Optionally, the apparatus may comprise an additional open end (not shown) which may be inserted orally i.e. into the mouth of the patient, or attached to a face mask.

Using the delivery of oxygen as an exemplary embodiment, during simple operation of the apparatus for the delivery of oxygen to a patient, oxygen is delivered from $O_2$ source 20 to delivery tube 10 through optional valve 30, which will direct the flow of oxygen from $O_2$ source 20 into delivery tube 10. In this mode or operation, valve 31 is opened to allow the $O_2$ to flow through branch 11B, as well as into branch 11A, and thus to be delivered through open ends 12A and 12B into the nostrils of the patient. Humidity source 40 may also supply moisture to the $O_2$ stream via port 41, and the mixing of oxygen and moisture may be controlled or adjusted via valve 30. In addition, heat source 50 (which may be incorporated into humidity source 40 as shown, or may be separate) may be used to heat the $O_2$ stream.

During delivery of a submicrometer drug aerosol according to the methods of the invention, delivery of $O_2$ as described above may be continued but only to one nostril. To make this change, valve 31 is closed, causing the flow of oxygen to take place only through branch 11A and open end 12A. In this mode, delivery tube 60 becomes active. Delivery tube 60 is connected to humidity source 40 and heat source 50 and also to nebulizer 70. Delivery line 60 receives a gaseous carrier of a predetermined temperature and a relatively low relative humidity (e.g. via port 42), and delivers the gaseous carrier to nebulizer 70. Nebulizer 70 generates a particle or droplet aerosol containing the therapeutic agent and optionally a hygroscopic excipient which mixes with the gaseous carrier and then flows into and through delivery tube 80. If a hygroscopic excipient is used, combination particles are formed if the droplets are dried sufficiently. Continuous or pulsated nebulization could be employed to synchronize drug aerosol nebulization with the patient's inspiratory effort using breath actuation apparatus. The opening of valve 32 causes ingress of the drug aerosol-laden carrier from delivery tube 80 into branch 11B of the system, and then into and out of open end 12B and into the patient's nostril. The patient thus receives simultaneously 1) relatively high RH, heated $O_2$ through open end 12A and 2) a gaseous stream of relatively low RH, heated aerosolized therapeutic agent through open end 12B. The provision of various valves and switches, and breath actuated nebulization in the apparatus avoids the need to disconnect the nasal cannula from the patient and greatly simplifies administration of the therapeutic, while also provided improved delivery of the therapeutic to the lungs.

While in some embodiments, during aerosol administration, the relatively high humidity gas that is delivered to the patient is oxygen, this need not always be the case. For example, moist, heated air may be delivered through delivery tube 10, or other gases combined with oxygen to increase water vapor content. If oxygen is delivered, it may be of any suitable concentration, e.g. from about 10% to about 100%. Further, in some embodiments, the lower relative humidity gas stream that carries the aerosol may be air, but may also be a stream of e.g. oxygen, or of helium and oxygen, or another gas to facilitate the formation of a submicrometer aerosol.

The apparatus of the invention may be used in conjunction with the delivery of e.g. oxygen, or may be used simply as a convenient, efficient, effective way to deliver substances of interest to the lungs of a patient, with or without $O_2$ therapy. For example, the apparatus may be used to deliver anesthesia, aerosolized antibiotics, anticancer chemotherapy agents, anti-asthmatics, and others (see below for a more comprehensive list), with or without the provision of oxygen.

In order to achieve suitable aerosol particle size growth and thus lung deposition, the moisture content of the streams is engineered to minimize growth in the nasal passages and maximize growth after mixing. The higher water vapor content stream is typically delivered above body temperature (or the temperature of the nasal airways) and at approximately 100% relative humidity (RH). Cooling of this stream through interactions with the airway walls produces supersaturated or near supersaturated conditions. The submicrometer aerosol stream is delivered either below body temperature, at RH values below 100%, or both. Further details regarding the moisture content of these streams is provided below. The gas that flows through the apparatus line that does not deliver aerosolized medicament (i.e. the second gaseous transport fluid, which is delivered by line 10 of FIG. 2, which may also be referred to as the "humidity line"), is generally of high relative humidity, e.g. in the range of from about 70% to about 110% and usually from about 95% to about 100%; and the temperature of the gas in this line is generally from about 20 to about 47° C., and usually from about 30 to about 42° C., e.g. ranging from about 21, 22, 23, 24, 25, 26, 27, 28, 29, 30, 31, 32, 33, 34, 35, 36, 37, 38, 39, 40, 41, 42, 43, 44, 45, or 46° C. to about 22, 23, 24, 25, 26, 27, 28, 29, 30, 31, 32, 33, 34, 35, 36, 37, 38, 39, 40, 41, 42, 43, 44, 45, 46 or 47° C. Further, the rate of gas flow in this line is generally in the range of from about 0.1 to about 90 L/min and usually from about 5 to about 30 L/min for adults. These flow rates are reduced as needed for delivery to animals and children.

The gas that flows through the apparatus lines that deliver aerosolized medicament in a first gaseous transport or carrier fluid (e.g. lines 60 and 80 of FIG. 2, which may also be referred to as first and second "aerosol lines"), is generally of subsaturated relative humidity, e.g. in the range of from about 0 to about 100% and usually from about 70 to about 99%. The temperature of the gas in this line is generally from about 20 to about 47° C., and usually from about 21 to about 32° C., e.g. ranging from about 20, 22, 23, 24, 25, 26, 27, 28, 29, 30, 31, 32, 33, 34, 35, 36, 37, 38, 39, 40, 41, 42, 43, 44, 45, or 46° C. to about 21, 23, 24, 25, 26, 27, 28, 29, 30, 31, 32, 33, 34, 35, 36, 37, 38, 39, 40, 41, 42, 43, 44, 45, 46 or 47° C. Further, the rate of gas flow in this line is generally in the range of from about 0.1 to about 90 L/min and usually from about 5 to about 30 L/min for adults. These flow rates are reduced as needed for delivery to animals and children.

Temperature and relative humidity values generally refer to the temperature and relative humidity of the stream(s) upon initial entry into the nostril (nasal inlet) of a subject to whom the gaseous streams are administered.

The initial size of the aerosolized particles or droplets that are generated by the nebulizer are generally in the range of from about 50 to about 1000 nm, (e.g. up to about 900, 925, 950, 975 or even 999 nm), and usually in the range of from about 100 to about 900 nm. Generally, these aerosol particles or droplets, when administered via an apparatus as described herein, grow to a size in the range of from about 1 to about 10 μm, and usually from about 2 to about 5 μm (e.g. 1, 2, 3, 4, 5, 6, 7, 8, 9, 10 or more μm), or to at least about 2 μm, to allow efficient deposition in the lung, and to avoid exhalation. In some embodiments, particles or droplets that contain one or more hygroscopic agents, as described above, are delivered.

Various nebulizers which can generate aerosols of this size are known to those of skill in the art, and include, for example, the Aeroneb® Pro (Aerogen), which contains a breath actuated mesh aerosol generator; the LC® Jet Plus (PARI Respiratory Equipment, Inc., Monterey, Calif.), T-Updraft® II (Hudson Respiratory Care Incorporated, Temecula, Calif.), Pulmo-Neb™ (DeVilbiss® Corp. Somerset, Pa.), Acorn-1 and Acorn-II (Vital Signs, Inc., Totowa, N.J.), Sidestream® (Medic-Aid, Sussex, UK) MicroAir® (Omron Healthcare, Inc., Vernon Hills, Ill.) and UltraNeb 99 (DeVilbiss® Corp. Somerset, Pa.). Other handheld devices include the eFlow® (PARI Respiratory Equipment, Inc., Monterey, Calif.), eFlow® Baby (PARI Respiratory Equipment, Inc., Monterey, Calif.), AeroNeb® (Aerogen, Inc., Mountain View, Calif.), Aero Dose™ (Aerogen, Inc., Mountain View, Calif.), AERx™ (Aradigm, Hayward, Calif.), Halolite™ (Profile Therapeutics Inc., Boston, Mass.), MicroAir® (Omron Healthcare, Inc., Vernon Hills, Ill.), TransNeb™ (Omron Healthcare, Inc., Vernon Hills, Ill.), and others that are known to those of skill in the art.

Those of skill in the art will recognize that various other arrangements of the elements depicted in FIG. 2 may be made and still result in an apparatus that delivers an aerosol as described herein, i.e. via a "dual stream nasal delivery" approach. For example, a nebulizer may be "built in" to a humidity/heat source; multiple heat or humidity sources may be connected to the delivery lines; instead of using valves to control the air flow, tubing may be completely disconnected or unplugged from the system (so long as the resulting aperture is blocked). Further, various monitors, gauges and/or meters may be incorporated to monitor, for example, the amount, pressure, flow rate, etc. of the gases that are employed; the temperature; the humidity (e.g. a hygrometer). A feedback system may be included that controls the heat supplied to the system to provide a constant temperature at the patient interface to maintain performance of the system and improve patient comfort. In addition, the apparatus may be part of a larger system such as a heart monitoring system, emergency care systems, (e.g. where acute care is required, as in an emergency vehicle such as an ambulance, or in a hospital emergency room); in an operating theatre; etc. Alternatively, the apparatus may be designed for use in more private settings such as in the home, or in short and long term care facilities where acute care in not necessary but where ongoing therapy is provided. The method and apparatus are suitable for use in e.g. high flow therapy (HFT), where usually from about 6 to up to about 40 liters/minute of gas is administered for adults. Values for infants and children are much lower (e.g., about 1 or 0.5 liter/min). The duration of therapy will depend upon the therapeutic agent being delivered together with the dose required. It is envisaged that this invention will permit both frequent short term administration and long term administration. Other possible applications of the technology also exist. For example, for NPPV therapy, which occurs largely through a face mask or via the mouth, the apparatus is adapted so that mixing of the two streams of air occurs as near the back of the throat as possible, e.g. air currents within the mask are designed to direct separate aerosol and humidity streams to different nostrils. The method and apparatus may be used in both the situation in which the patient can breathe on his/her own, and when he/she cannot do so. One advantage of the nasal delivery route as compared to oral aerosol delivery route is that the patient retains the ability to talk, eat, drink, etc. even while medications are administered.

Substances that are suitable for delivery using the methods and apparatus of the invention are listed below in section III, and also include those listed in U.S. Pat. Nos. 7,726,308 and 5,126,123 (and references cited therein), the complete contents of which are herein incorporated by reference.

III. Types of Therapeutic Agents that May be Formulated to Include a Hygroscopic Excipient and/or which May be Delivered by the Dual-Delivery System of the Invention Substances (e.g. drugs, therapeutic agents, active agents, etc.) that may be formulated with a hygroscopic excipient as described herein or delivered as described herein include but are not limited to various agents, drugs, compounds, and compositions of matter or mixtures thereof that provide some beneficial pharmacologic effect. The particles of the invention broadly encompass substances including "small molecule" drugs, vaccines, vitamins, nutrients, aromatherapy substances, and other-beneficial agents. As used herein, the terms further include any physiologically or pharmacologically active substance that produces a localized or systemic effect in a patient, i.e. the agent may be active in the lung, or may be delivered to the lung as a gateway to systemic activity.

In some embodiments, the site of action of the substance that is delivered may be the lung itself. Examples of such agents include but are not limited to agents for anesthesia; treatments for asthma or other lung conditions; anti-viral, anti-bacterial or anti-fungal agents; anti-cancer agents; α-1 antitrypsin and other antiproteases (for congenital deficiencies), rhDNAse (for cystic fibrosis), and cyclosporine (for lung transplantation), vaccines, proteins and peptides, etc. Other examples include bronchodilators including albuterol, terbutaline, isoprenaline and levalbuterol, and racemic epinephrine and salts thereof; anti-cholinergics including atropine, ipratropium bromide, tiatropium and salts thereof; expectorants including dornase alpha (pulmozyme) (used in the management of cystic fibrosis; corticosteroids such as budesonide, triamcinolone, fluticasone; prophylactic anti-asthmatics such as sodium cromoglycate and nedocromil sodium; anti-infectives such as the antibiotic gentamicin and the anti-protozoan pentamidine (used in the treatment of *Pneumocystis carinii* pneumonia), and the antiviral agent ribavirin, used to treat respiratory syncytial virus e.g. in young children and infants.

However, this need not be the case. Some agents delivered via the deep lung into systemic circulation will be distributed systemically via the circulatory system. Examples of such agents include but are not limited to, for example, calcitonin (for osteoporosis), human growth hormone (HGH, for pediatric growth deficiency), various hormones such as parathyroid hormone (PTH, for hyperparathyroidism), insulin and other protein or peptide agents, nucleic acid molecules, and anti-pain or anti-inflammation agents. Such agents may require chronic administration. The ability of the invention to deliver these often expensive agents at higher delivery efficiencies to the deep lung where they are systemically absorbed is a significant advantage over conventional aerosol drug delivery methods including metered dose inhalers, dry powder inhalers and nebulizers.

In another example, it may be desirable to target areas for the lungs to delivery of therapeutic agents. In this example, anti-infective agents may be required to treat localized lung infections within the airways. Targeting to specific regions within the lung and delivering drug aerosols with high deposition efficiencies is possible with this invention. Once a target region has been identified (through clinical examination), an aerosol would be produced that would have a final particle size suitable for deposition in that region. In this example, an initially nano-sized aerosol would be formulated with appropriate hygroscopic excipients and inhaled. By controlling the amount of hygroscopic excipients present in the aerosol formulation, it is possible to control the final particle size of the aerosol and therefore ultimately its site of deposition within the lung.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (aziocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefinenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; glycopeptides, inlcuding vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofluvin, tonoftal, naftifin, terbinafin, amorolfin, ciclopiroxolamin, echinocandins, such as micafungin, caspofungin, anidulafungin; nitrofurans, including nitrofurantoin and nitrofuranzone; -polyenes, including amphotericin B, natamycin, nystatin, flucocytosine; other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine; antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors; plant extracts or ingredients, such as plant extracts from chamomile, hamamelis, echinacea, *calendula*, papain, pelargonium, essential oils, myrtol, pinen, limonen, cineole, thymol, mentol, alpha-hederin, bisabolol, lycopodin, vitapherole; wound healing compounds including dexpantenol, allantoin, vitamins, hyaluronic acid, alpha-antitrypsin, anorganic and organic zinc salts/compounds, interferones (alpha, beta, gamma), tumor necrosis factors, cytokines, interleukins.

In a similar way to that described for targeting antibiotics, it may also be desirable to target anti-cancer compounds or chemotherapy agents to tumors within the lungs. It is envisaged that by formulating the agent with an appropriate hygroscopic growth excipient, it will be possible to target regions of the lung where it has been identified that the tumor is growing. Examples of suitable compounds are immunmodulators including methotrexat, azathioprine, cyclosporine, tacrolimus, sirolimus, rapamycin, mofetil, cytotatics and metastasis inhibitors, alkylants, such as nimustine, melphanlane, carmustine, lomustine, cyclophosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinum, cis-platinum and metallocene compounds such as titanocendichloride; amsacrine, dacarbazine, estramustine, etoposide, beraprost, hydroxy-carbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab may be added.

Additional active agents may be selected from, for example, hypnotics and sedatives, tranquilizers, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents (particularly those that target lung cancer), antithrombotic agents, antihypertensives, cardiovascular drugs, antiarrhythmics, antioxicants, hormonal agents including contraceptives, sympathomimetics, diuretics, lipid regulating agents, antiandrugenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically. The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of other active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., monoacylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, and 13-cis retinoic acid, and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof. Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense and inhibitory RNA. Further, an active agent may comprise live attenuated or killed viruses suitable for use as vaccines. Other useful drugs include those listed within the Physician's Desk Reference (most recent edition).

An active agent for delivery or formulation as described herein may be an inorganic or an organic compound, including, without limitation, drugs which act on: the lung, the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Frequently, the active agent acts in or on the lung.

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of hygroscopic excipient contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

In addition to one or more active agents and hygroscopic excipient(s), the aerosol particles/droplets may optionally include one or more pharmaceutical excipients (which differ from the hygroscopic excipients) that are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients serve to further improve the features of the active agent composition, for example by improving the handling characteristics of powders, such as flowability and consistency, and/or facilitating manufacturing and filling of unit dosage forms. One or more excipients may also be provided to serve as bulking agents when it is desired to reduce the concentration of active agent in the formulation. Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers. The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextr-in), polyethylene glycols, and pectin. The particles may further include inorganic salts, antimicrobial agents (for example benzalkonium chloride), antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations).

Drug substances that are particularly suitable for delivery using a hygroscopic excipient are generally particularly hydrophobic and/or that have a very low intrinsic capability to take on water. Such substances include but are not limited to corticosteroids, e.g. budesonide, fluticasone, triamcinolone and salts thereof; as well as certain benzodiazepines e.g. lorazepam, oxazepam, and temazepam.

The delivery systems and formulations of the invention are generally suitable for treating animals, usually mammals. The mammal may be a human, but this is not always the case; veterinary applications and applications where animals are used to assess aerosol exposures to drugs and pollutants are also encompassed by the invention.

EXAMPLES

These Examples describe experimental data as follows:

Examples 1-3, the use of a hygroscopic excipient to promote lung deposition of aerosols;

Examples 4-7, the dual delivery stream technology.

Example 1

Budesonide Nanoparticles

Budesonide nanoparticle aerosols were generated using the Capillary Aerosol Generator (CAG). This technology represents a generic means of producing engineered pharmaceutical nanosized particles suitable for inhalation. The CAG utilizes controlled heating of a liquid formulation passing through a capillary tube to produce nanosized dry particles exiting the capillary nozzle.

Table 1 shows the formulations that were employed to produce drug-hygroscopic excipient nanoparticles. In this example, nanoparticles were produced from solutions in ethanol/water, the ratio of which varied depending on individual solubilities of drug and excipient, together with the desired nanoparticle size. Nanoparticle size is controlled by a number of parameters including the proportion of ethanol/water (within the solubility limits), the total solid content (drug and excipient), the CAG aerosolization conditions (formulation flow rate, applied heating energy, capillary exit diameter).

Table 1 shows the mass median aerodynamic diameters (MMAD) and particle size growth ratios for budesonide nanoparticles generated using the CAG. The mean initial MMAD for the budesonide nanoparticles containing drug alone was 430 nm. Similar values were observed when nanoparticles containing budesonide and sodium chloride (50/50 w/w) and budesonide and sorbital (50/50 w/w) were generated indicating that the incorporation of the hygroscopic excipient did not significantly affect the initial size of the nanoparticles.

TABLE 1

Hygroscopic growth properties of budesonide nanoparticles formulated with a hygroscopic growth excipient (n = 4, except * where n = 1).

| Solution Formulation | Nanoparticle | Initial MMAD | Final MMAD (99% RH) | Growth ratio |
|---|---|---|---|---|
| 0.15% Budesonide in ethanol/water (50/50% v/v) | Budesonide (100%) | 430 nm | 480 nm | 1.11 |
| 0.1% Budesonide and 0.1% sodium chloride in ethanol/water (50/50% v/v) | Budesonide and sodium chloride (50/50% w/w) | 490 nm | 980 nm | 2.26 |
| 0.4% Budesonide and 0.1% sodium chloride in ethanol/water (90/10% v/v)* | Budesonide and sodium chloride (80/20% w/w) | 500 nm | 770 nm | 1.77 |
| 0.125% Budesonide and 0.125% sorbital in ethanol/water (50/50% v/v) | Budesonide and sorbital (50/50% w/w) | 500 nm | 820 nm | 1.88 |

Hygroscopic growth of these nanoparticle aerosols was evaluated by passing the aerosol through a growth tube. Briefly, following nanoparticle generation the aerosols were drawn through the 29 cm hygroscopic growth tube at a flow rate of 30 L/min. The tube was held at 37° C. and 99% relative humidity (RH) to simulate expected lung conditions. The growth tube was approximately 29 cm, which is consistent with the distance from the mouth inlet to the main bronchi of an adult. Following passage through the tubular geometry the aerosols were delivered to the 10-stage MOUDI or Andersen Cascade Impactor (ACI; Graseby-Andersen Inc, Smyrna, Ga.) for particle sizing. Both the tubular geometry and the cascade impactor were placed in an environmental chamber (Espec Environmental Cabinet, Hudsonville, Mich.) to maintain constant temperature and humidity conditions. The ACI was employed following hygroscopic growth when it was expected that the aerosols produced would be in the 1-3 μm size range. For these studies, the final aerodynamic particle size distribution of the aerosol exiting the hygroscopic growth tube was determined at 28±2 L/min, and humidified co-flow air (99% RH) was supplied to the impactor. Following aerosol generation, washings were collected from the impaction plates to determine the drug deposition using a suitable solvent. The solutions were then assayed using validated HPLC-UV methods for the drug. The mass of drug on each impaction plate was determined and used to calculate both the initial and final aerodynamic particle size distributions of the drug aerosols. The growth ratios were calculated by comparing the final size with the initial size of the nanoparticle as a measure of hygroscopic size increase.

As can be seen from the data presented in Table 1, here was no significant change in the particle size distribution of the budesonide nanoparticles without excipient following transit through the humidified growth tube. Budesonide is a hydrophobic drug with poor water solubility and would not be expected to exhibit hygroscopic growth. The addition of sodium chloride, at a 50% w/w ratio, to the budesonide nanoparticle did not cause a significant change in the initial size of the nanoparticle, however, a significant particle size growth was observed following exposure to 99% RH during passage though the growth tube. A growth ratio of 2.26 was observed over this relatively short duration of passage (0.2 s) through the growth tube. A decrease in the amount of sodium chloride in the nanoparticle was accompanied by a decrease in the observed particle size growth, demonstrating the ability to control the amount of growth by altering the amount of hygroscopic excipient or the ratio of drug and hygroscopic excipient formulated in the nanoparticle. Nanoparticles containing budesonide/sodium chloride (80/20% w/w) had a growth ratio of 1.77.

Budesonide and sorbital nanoparticles (50/50% w/w/) also showed a significant size increase in the growth tube. A growth ratio of 1.88 was observed, although as expected the growth ratio was slightly lower compared to the budesonide/sodium chloride nanoparticles. This demonstrates further the ability to control the amount of particle size growth by selecting a different hygroscopic excipient. These results demonstrate that the inclusion of a hygroscopic excipient can be employed to alter the aerodynamic particle size characteristics of nanoparticles following exposure to temperature and humidity conditions designed to simulate the human airways. Furthermore, Example 3 (below) demonstrates that particle size growth is still occurring after 0.2 s and continues through a typical respiratory exposure period of 2 s producing even larger growth ratios. Those skilled in the art will recognize that the exemplary initial nanoparticle size, % composition and type of excipient employed only provide a few examples of potential combinations that could be employed in the practice of the present invention.

Example 2

Albuterol Nanoparticles

Albuterol (base) and albuterol sulfate nanoparticle aerosols were also generated using the Capillary Aerosol Generator (CAG). Albuterol (base) is poorly water soluble, in contrast to the freely soluble sulfate salt of albuterol.

Table 2 shows the formulations that were employed to produce drug-hygroscopic excipient nanoparticles. In this example, nanoparticles were produced from solutions in ethanol/water, the ratio of which varied dependent upon individual solubilities of drug and excipient, together with the desired nanoparticle size. Nanoparticle size is controlled by a number of parameters including the proportion of ethanol/water (within the solubility limits), the total solid content (drug and excipient), the CAG aerosolization conditions (formulation flow rate, applied heating energy, capillary exit diameter).

Table 2 shows the mass median aerodynamic diameters (MMAD) and particle size growth ratios for albuterol nanoparticles generated using the CAG. The mean initial MMAD for the albuterol sulfate nanoparticles containing drug alone was 380 nm, and slightly larger values were observed for the initial mean diameters of the drug—hygroscopic excipient nanoparticles.

TABLE 2

Hygroscopic growth properties of albuterol nanoparticles formulated with a hygroscopic growth excipient (n = 3-4).

| Solution Formulation | Nanoparticle | Initial MMAD | Final MMAD (99% RH) | Growth ratio |
|---|---|---|---|---|
| 0.2% Albuterol sulfate in ethanol/water (50/50% v/v) | Albuterol sulfate (100%) | 380 nm | 510 nm | 1.35 |
| 0.1% Albuterol sulfate and 0.1% sodium chloride in ethanol/water (50/50% v/v) | Albuterol sulfate & sodium chloride (50/50% w/w) | 490 nm | 930 nm | 2.20 |
| 0.1% Albuterol (base) and 0.1% sodium chloride in ethanol/water (50/50% v/v) | Albuterol sulfate & sodium chloride (50/50% w/w) | 460 nm | 890 nm | 2.37 |

Hygroscopic growth of these nanoparticle aerosols was evaluated by passing the aerosol through a growth tube as described in Example 1. In addition, for a series of experiments with the albuterol sulfate/sodium chloride (50/50% w/w) nanoparticles, the hygroscopic grow tube was extended in length to 87 cm (three times the original length). The resulting particle residence time is approximately 0.6 seconds, which is approximately one third of an average inhalation cycle.

As can be seen in Table 2, the drug only nanoparticles containing albuterol sulfate had a modest growth ratio (1.35), indicative of the limited growth that would occur when drug only nanoparticles are delivered to the respiratory tract. It should be noted that the growth for the albuterol sulfate particles was larger than was observed for the budesonide only nanoparticles in Example 1. Albuterol sulfate is a hydrophilic molecule compared to budesonide, which is hydrophobic. The addition of sodium chloride, at a 50% w/w ratio, to the albuterol sulfate nanoparticle did cause a significant increase in the measured particle size following exposure to 99% RH during passage though the growth tube. A growth ratio of 2.20 was observed over this relatively short duration of passage through the growth tube. This result indicates that the addition of a hygroscopic excipient to the albuterol sulfate nanoparticle was capable of producing a significant growth above what was observed from drug alone. Increasing the length of the growth tubing was observed to further increase the size of the final aerosol for the albuterol sulfate/sodium chloride (50/50% w/w) nanoparticles. The particles increased to 1070 nm following passage through the 87 cm tube, which was a growth ratio of 2.85.

The growth observed for albuterol base/sodium chloride (50/50% w/w) nanoparticles was similar to that observed for the albuterol sulfate/sodium chloride (50/50% w/w) nanoparticles. This is evidence that the hygroscopic growth potential of the nanoparticles is primarily dependent upon the excipient rather than the drug molecule. Those skilled in the art will recognize that the exemplary initial nanoparticle size, % composition and type of excipient employed only provide a few examples of potential combinations that could be employed in the practice of the present invention.

Example 3

Development of a Mathematical Model of Aerosol Size Increase for Hygroscopic Excipients and Combination Excipient-Drug Particles The objective of this study was to develop a validated mathematical model of aerosol size increase for hygroscopic excipients and combination excipient-drug particles and to apply this model to characterize growth under typical respiratory conditions. The model includes full coupling between the aerosol and vapor phase and between the air phase and respiratory walls. The validation study was performed by comparing model predictions to experimentally measured values of aerosol particle size growth for both drug and hygroscopic excipient-drug combination particles after a specific exposure period to simulated human respiratory tract temperature and humidity conditions. The model was then applied to determine the effects of hygroscopic characteristics, particle parameters, and aerosol properties on growth for typical respiratory exposure conditions. Functional relationships were sought to characterize the complex interconnections of the relevant variables and thereby dramatically simplify the growth predictions. These functional relationships will help to identify the parameters most responsible for aerosol size increase. Moreover, these relationships can be used to engineer particle characteristics to achieve a desired level of size change and thereby target deposition within specific regions of the airways.

Methods

Experimental Design

Figure 3:
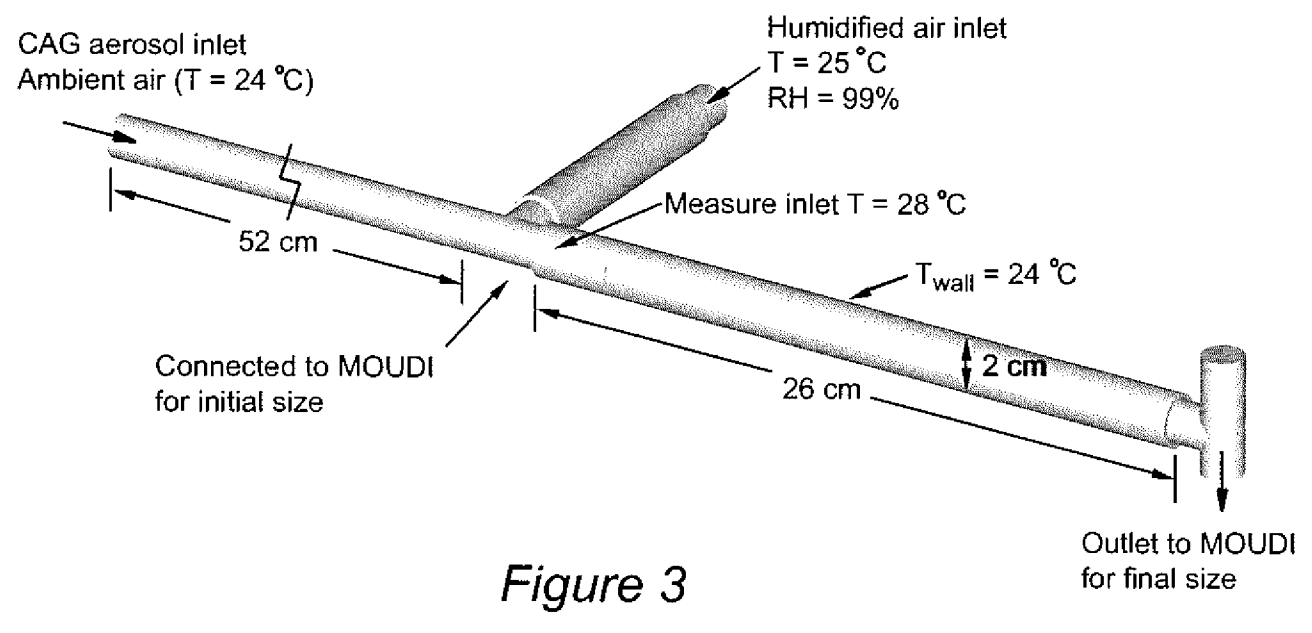

For experimental validation of the numerical model, a test system was constructed as shown in FIG. 3. Submicrometer drug and drug-hygroscopic excipient particles were formed using a capillary aerosol generator (CAG). The capillary aerosol generation system is described and considered in detail by the previous studies of Hindle et al. (1998) and Longest et al. (2007). In the current study, the formulation was a mixture of 50% water and 50% ethanol by weight to dissolve both hydrophilic and hydrophobic drugs. This solution was heated and pumped through the CAG at a flow rate of 10 mg/s to form the spray aerosol. Single drug and drug-hygroscopic excipient particles were created experimentally for albuterol sulfate (AS), budesonide (BD), and sodium chloride (NaCl). Specifically, single component drug particles were formed using a 0.2% w/v AS solution and a 0.15% w/v BD solution, respectively. Combination drug-hygroscopic excipient particles were generated using a 0.1% AS-0.1% NaCl w/v solution and a 0.1% BD-0.1% NaCl w/v solution, respectively. The spray aerosol was allowed to dry into solid particles by passage through a 52 cm length of dry tubing (FIG. 3). Initial particle size was then assessed by connecting the tubing to a 10 stage MOUDI (MSP Corp, Shoreview, Minn.). To produce growth, the aerosol stream was combined with humidified air at T=25° C. and RH=99% sampled from an environmental cabinet. The combined mixture had a flow rate of approximately 30±2 L/min and was passed through a 26 cm length of tubing (the growth zone) with a diameter of 2 cm. This length was selected to provide a residence time of approximately 0.2 s, which is consistent with the time required for an orally inhaled pharmaceutical aerosol to reach the main bifurcation of the lungs under standard inhalation conditions. Walls of the growth section were pre-wetted to simulate the wet walled conditions of the respiratory tract, which stimulates aerosol growth. The growth tube was not heated and was exposed to 24° C. room temperature air for this initial validation experiment. After exiting the growth tube, the aerosol was passed into the 10 stage MOUDI for size characterization.

In separate experiments, the temperature and humidity of the humidified air and the temperature of the aerosol mixture stream at the inlet to the condensational growth tube were measured. These measurements were performed using the Humicap Handheld Meter (HMP75B, Vaisala, Helsinki, Finland) positioned at the mid-plane of the tubing and a sheathed Type K thermocouple (Omega Engineering Corp., Stamford, Conn.) positioned at the mid-plane of the tubing. The Humicap Handheld Meter has a stated temperature accuracy of ±0.2° C. (at 20° C.) and ±0.25° C. (at 40° C.). It has a RH accuracy of ±1.7% (at 20° C.) and ±1.8% (at 40° C.) between 90-100% RH. The probe was factory calibrated using traceable standards and supplied with a NIST calibration certificate. The probe was housed in a plastic filter and incorporated a sensor pre-heater which was employed to prevent condensation during equilibration prior to measurement and had a response time of 17 s in still air. In all cases, experimental duration (>30 s) was sufficient to allow equilibration of the probes.

The initial aerodynamic particle size distribution of the aerosol exiting the drying section of tubing was determined using the 10 stage MOUDI operated at 30±2 L/min, which allowed size fractionation between 50 nm and 10 µm. Humidified co-flow air (99% RH) was supplied to the impactor which was placed in the environmental chamber and held at constant temperature and humidity conditions of 25° C. and 99% RH. The final aerodynamic particle size distribution of the aerosol exiting the condensational growth tube was also determined using the MOUDI operated at 30±2 L/min. For both the initial and final particle size distributions, following aerosol generation, washings were collected from the impaction plates to determine the drug deposition. A 1:1 admixture (25 mL total) of methanol and deionized water was used, and the solutions were then assayed using a validated HPLC-UV method for AS and BD. The mass of drug and excipient on each impaction plate was determined and used to calculate both the initial and final aerodynamic particle size distributions of the drug and combination aerosols. Aerosol droplet size distributions were reported as mass distribution recovered from the impactor. The mass median aerodynamic diameter (MMAD) was defined as the particle size at the 50th percentile on a cumulative percent mass undersize distribution (D50) using linear interpolation. Four replicates of each experiment were performed.

Numerical Model and Solution

The numerical model considers a group of monodisperse droplets with number concentration $n_{part}$ flowing in the in vitro system or respiratory airways. Well mixed conditions are assumed at each time level, which is equivalent to considering radially constant conditions at each depth of penetration into the respiratory model, i.e., a 1-D approach. Heat and mass transfer are considered between the droplets and air phase and between the air and wall. The interconnected first order non-linear differential equations governing the droplet temperature ($T_d$), droplet radius ($r_d$), air temperature ($T_{air}$), and water vapor mass fraction in the air ($Y_{v,air}$) are $$\frac{dT_d}{dt} = \frac{3}{\rho_d Cp_d r_d}(-\bar{q}_d - L_v \bar{n}_d) \quad (1)$$

$$\frac{dr_d}{dt} = \frac{-\bar{n}_d}{\rho_w} \quad (2)$$

$$\frac{dT_{air}}{dt} = \frac{4\pi r_d^2}{\rho_{air} Cp_{air}} \bar{q}_d n_{part} + \frac{\bar{q}_{wall}}{\rho_{air} Cp_{air}} \frac{4}{D_{tube}} \quad (3)$$

$$\frac{dY_{v,air}}{dt} = \frac{4\pi r_d^2}{\rho_{air}} \bar{n}_d n_{part} + \frac{\bar{n}_{wall}}{\rho_{air}} \frac{4}{D_{tube}} \quad (4)$$

In these expressions, ρ and Cp are the densities and specific heats of the droplet (d), air, and water (w). The first equation describes droplet temperature change based on convective ($\bar{q}_d$) and evaporating ($L_v \bar{n}_d$) heat fluxes at the droplet surface. In this expression, $L_v$ represents the latent heat of water vaporization and $\bar{n}_d$ is the evaporating or condensing mass flux at the surface. Overbars on the flux values indicate area-averages taken over the droplet surface, based on the rapid mixing assumption (Longest and Kleinstreuer 2005). Equation (2) describes the rate of droplet size change as a function of surface mass flux. The third equation describes the well mixed air temperature at each time, which is controlled by the convective flux from the droplet and the heat flux from the walls ($\bar{q}_{wall}$) for a tube with a characteristic diameter $D_{tube}$. The mass fraction of water vapor in the air ($Y_{v,air}$) is influenced by the mass gained or lost at the droplet surface and the wall mass flux ($\bar{n}_{wall}$).

The flux components at the droplet surface in Eqs. (1-4) can be defined as $$\bar{q}_d = \frac{Nu \kappa_{air} C_T}{2r_d}(T_d - T_{air}) \qquad (5)$$

$$\bar{n}_d = \rho_{air} \frac{Sh \tilde{D}_v C_M}{2r_d} \frac{Y_{v,surf} - Y_{v,air}}{1 - Y_{v,surf}} \qquad (6)$$

In the convective flux term, Nu is the Nusselt number, $\kappa_{air}$ is the thermal conductivity of the gas mixture, and $T_{air}$ is the temperature condition surrounding the droplet. The term $C_T$ represents the Knudsen correlation for non-continuum effects, which is negligible for the sizes considered here ($C_T$=1.0). Both $T_d$ and $T_{air}$ are variable, and determined by Eqs. (1) and (3), respectively. Due to the small droplet size and associated small particle Reynolds number, the Nusselt number is defined as Nu=2.0, from the correlation of Clift et al. (1978). For the mass flux expression, Eq. (6), Sh is the non-dimensional Sherwood number, $\tilde{D}_v$ is the binary diffusion coefficient of water vapor in air, and $Y_{v,surf}$ is the water vapor mass fraction at the surface of the droplets. This expression includes the effect of droplet evaporation on the evaporation rate, which is referred to as the blowing velocity (Longest and Kleinstreuer 2005). In Eq. (6), $C_M$ is the mass Knudsen number correction, which is equivalent to one as with $C_T$.

Flux values at the wall can be expressed as $$\bar{q}_{wall} = \frac{Nu_{wall} \kappa_{air}}{D_{tube}}(T_{wall} - T_{air}) \qquad (7)$$

$$\bar{n}_{wall} = \rho_{air} \frac{Sh_{wall} \tilde{D}_v}{D_{tube}}(Y_{v,wall} - Y_{v,air}) \qquad (8)$$

Considering the wall heat flux, Eq. (7), the wall temperature ($T_{wall}$) is held constant. The geometry is assumed to be cylindrical with a characteristic diameter of $D_{tube}$. It is expected that a majority of droplet growth will occur in distal lung regions, where the flow can be considered laminar and fully developed. Under these conditions, the wall Nusselt number has a constant value of $Nu_{wall}$=3.66. Similarly in the mass flux expression, $Y_{v,wall}$ assumed constant for either dry or wet walls and the Sherwood number is $Sh_{wall}$=3.66.

Considering variable particle and flow field properties, the densities dens of the multicomponent droplets are calculated as $$\rho_d = (m_w + m_{drug} + m_{ex})\left(\frac{\rho_w}{m_w + \frac{m_{drug}\rho_w}{\rho_{drug}} + \frac{m_{ex}\rho_w}{\rho_{ex}}}\right) \qquad (9)$$

In this expression, m and ρ are the masses and densities of water (w), drug, and hygroscopic excipient (ex). The binary diffusion coefficient of water vapor used in Eqs. (6) and (8) is calculated from (Vargaftik 1975)

$$\tilde{D}_v = 2.16 \times 10^{-5}\left(\frac{T[K]}{273.15}\right)^{1.8} [m^2/s] \qquad (10)$$

The temperature dependent saturation pressure of water vapor is determined from the Antoine equation (Green 1997)

$$P_{v,sat} = \exp\left(23.196 - \frac{3816.44}{T[K] - 46.13}\right) [Pa] \qquad (11)$$

which is considered to be more accurate than the Clausius-Clapeyron relation across a broad range of temperatures. Relative humidity is calculated based on the saturation pressure of water vapor as follows $$RH = \frac{P_v}{P_{v,sat}} = \frac{Y_v \rho_{air} R_v T}{Y_{v,sat} \rho_{air} R_v T} = \frac{Y_v}{Y_{v,sat}} \qquad (12)$$

where $R_v$ is the gas constant of water vapor.

The mass fraction of water vapor on the droplet surface is a critical variable, which is significantly influenced by both temperature and solute concentration. For a combination particle of soluble drug and excipient, $Y_{v,surf}$ is calculated as $$Y_{v,surf} = \frac{SKP_{v,sat}(T_d)}{\rho_{air} R_v T_d} \qquad (13)$$

where $P_{v,sat}(T_d)$ is the temperature dependent saturation pressure of water vapor, calculated from Eq. (11). The influence of the Kelvin effect on the droplet surface concentration of water vapor is expressed as $$K = \exp\left[\frac{4\sigma(T_d)}{2r_d \rho_d R_v T_d}\right] \qquad (14)$$

where $\sigma(T_d)$ is the temperature dependent surface tension of the droplet. In Eq. (13), the water activity coefficient, S, describes how dissolved molecules affect the surface concentration of water vapor, i.e., the hygroscopic effect, and can be expressed as $$S = \left(1 + \frac{i_{drug} \chi_{drug} + i_{ex} \chi_{ex}}{\chi_w}\right)^{-1} \qquad (15)$$

for a drug and hygroscopic excipient combination particle where χ represents the mole fraction of each component. The i coefficients account for the effect of molecular dissociation during dissolution and are sometimes referred to as van't Hoff factors. At high concentrations of drug and excipient, the available water may not be sufficient to dissolve all of the material. In these cases, $\chi_{drug}$ and $\chi_{ex}$ are replaced by the mole fraction solubility limits of each compound in water. This approach assumes an initial droplet model of a solid core of un-dissolved material surrounded by a layer of liquid with a saturated concentration of each solute. This model persists until there is enough water to fully dissolve the drug and excipient. In either case, the mole fraction of water is calculated as $$\chi_w = 1 - \chi_{drug} - \chi_{ex} \quad (16)$$

It is noted that Eq. (15) has a form similar to Raoult's law and is valid for materials that may (i>1) or may not (i=1) dissociate upon dissolution. Specifically, Raoult's law provides a linear expression to describe activity coefficients at low solute concentrations, as presented by Finlay (2001). In contrast, the expression used in this study is non-linear and better describes activity coefficient data over a wide range of solute mole fractions. Use of Eq. (15) can be further justified by considering that the mole fractions of drug and excipient do not exceed the solubility limit of the material, which is low for most compounds considered in this study ($\chi_{sat} \leq 0.1$; Table 3). Furthermore, values of the i coefficients in this study are determined based on best fits to experimental data over a range of concentrations. Therefore, the application of Eq. (15) can be viewed as a physically based expression for fitting the experimental data. Finally, high accuracy is required at dilute concentrations, which have the largest impact on the final size achieved by the hygroscopic aerosol.

The resulting set of governing equations describing droplet heat and mass transfer was solved using a variable time-step accuracy-controlled coupled differential equation solver in the numerical package MathCAD 13 (Mathsoft Apps.). Reducing the accuracy control limit by an order of magnitude had a negligible (less than 1%) effect on the final predicted droplet and air phase variables.

Standard Respiratory Exposure Conditions

In this study, a fixed set of respiratory exposure conditions was selected to characterize particle size growth as a function of hygroscopic, particle, and aerosol characteristics. It is expected that a majority of growth during EEG occurs in distal lung regions. As a result, wall temperature and RH conditions were set to constant values of $T_{wall}=37°$ C. and $RH_{wall}=99.5\%$. A 2 s inhalation time was selected as a conservative exposure period. The governing equations of droplet heat and mass transfer can be applied within individual branches of the respiratory tract or within a representative geometry with a single characteristic diameter. The latter approach was selected for this study to simplify the calculations and form a well described system. The characteristic dimension was selected based on an airway diameter below which the aerosol spends 80% of its residence time in the lungs. To map residence times, the symmetric airway model of Weibel was considered and scaled to a functional residual capacity of 3.5 L. For an inhalation flow rate of 30 L/min, it was determined that 80% of the residence time occurs below the 19$^{th}$ generation, which has a diameter of 0.4 mm. This airway diameter is also representative of the entire alveolar region of the lungs (Haefeli-Bleuer and Weibel 1988) and was therefore used as the single characteristic airway diameter in the equations.

Cases Evaluated

The model is first validated based on the exposure conditions of the in vitro experiments. This study then seeks to determine the effects of hygroscopic, particle, and aerosol properties on EEG for a fixed set of respiratory parameters. Hygroscopic effects are evaluated by considering single component and combination particles of model drugs and hygroscopic excipients. Model drugs considered are AS and BD, which are typically thought to be hygroscopic and non-hygroscopic, respectively, based largely on solubility characteristics in water. For the evaluation of excipients, a representative salt (NaCl), sugar (mannitol—MN), weak acid (citric acid—CA), and liquid glycol (propylene glycol—PG) were selected. As shown in Table 4, these materials represent a range of molecular weights and solubilities, which are expected to affect the hygroscopicity of the particle/droplet (cf. Eq. 15). Initially, hygroscopic effects are assessed for fixed particle ($d_{initial}=500$ nm) and aerosol ($n_{part}=3.9\times10^5$ part/cm$^3$) parameters. Particle engineering and aerosol properties are then evaluated by modifying the initial diameters, drug and excipient mass fractions, and number concentrations.

TABLE 3

Hygroscopic properties of drugs and excipients.

| Compound | Density (ρ) kg/m$^3$ | Molar mass (M) kg/kmol | Saturated mass fraction (mf$_{sat}$)$^b$ | Saturated mole fraction ($\chi_{sat}$)$^c$ | Predicted van't Hoff factor (i) | Hygroscopic parameter i$_s\rho_s$/M$_s$ |
|---|---|---|---|---|---|---|
| Water | 997.0 | 18.0 | NA | NA | NA | NA |
| Albuterol sulfate (AS) | 1340. | 576.7 | 0.28 | 0.012 | 2.1d | 4.9 |
| Budesonide (BD) | 1000.$^a$ | 430.0 | Not soluble | Not soluble | NA | NA |
| Citric acid (CA) | 1665. | 192.1 | 0.57 | 0.11 | 1.9$^d$ | 16.5 |
| Mannitol (MN) | 1489. | 182.0 | 0.15 | 0.018 | 1.0$^e$ | 8.2 |
| Sodium chloride (NaCl) | 2165. | 58.4 | 0.265 | 0.10 | 2.1$^f$ | 77.9 |

TABLE 3-continued

Hygroscopic properties of drugs and excipients.

| Compound | Density (ρ) kg/m³ | Molar mass (M) kg/kmol | Saturated mass fraction $(mf_{sat})^b$ | Saturated mole fraction $(\chi_{sat})^c$ | Predicted van't Hoff factor (i) | Hygroscopic parameter $i_s \rho_s / M_s$ |
|---|---|---|---|---|---|---|
| Propylene glycol (PG) | 1036. | 76.1 | 1.00 | 1.00 | $1.0^d$ | 13.6 |

[a] Approximate value
[b] Mass fraction of compound that can be dissolved in liquid water at 25° C.
[c] Mole fraction of compound that can be dissolved in liquid water at 25° C.
[d] Measured in this study.
[e] Based on the measurements of Ninni et al. (2000).
[f] Based on the correlations of Cinkotai (1971).

Results
Calculation of i Coefficients

Figures 4A, 4B:
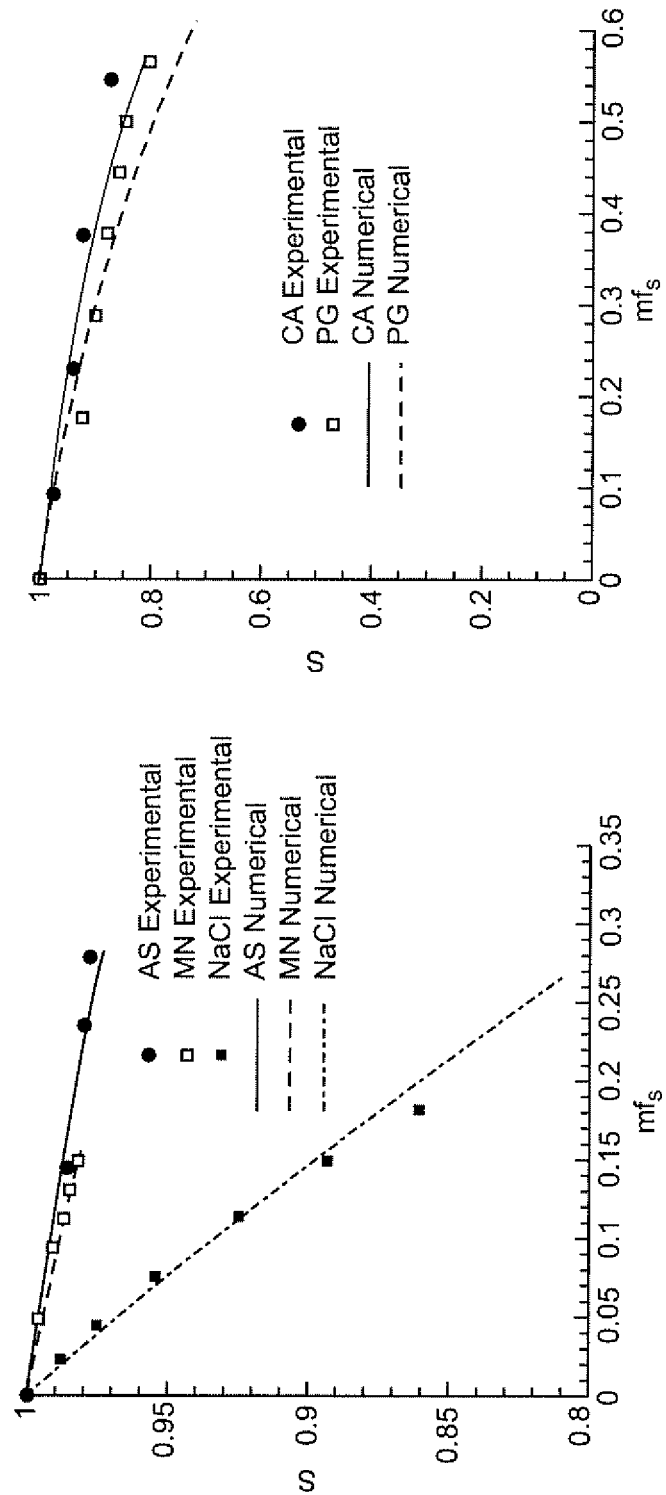
FIGS. 4A and B. Experimental and numerical predictions of activity coefficients (S) over a range of solute mass fractions in water at 25° C. for (A) moderately soluble and (B) highly soluble compounds.
Figure 5A:
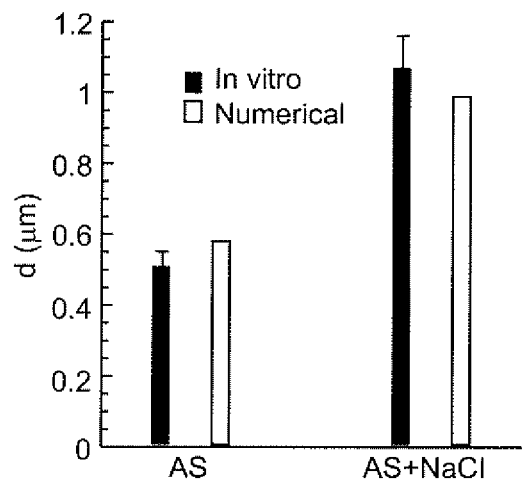
FIG. 5A-D. Final geometric diameter and diameter growth ratio based on in vitro results and numerical predictions of (A & B) AS and AS+NaCl combination particles and (C & D) BD and BD+NaCl combination particles. In all cases, the numerical predictions provide a good estimate to the in vitro results for conditions consistent with the experimental system.
Figure 5B:
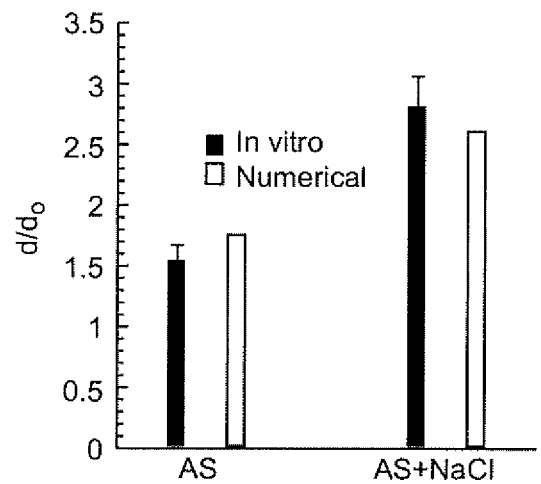
Figure 5C:
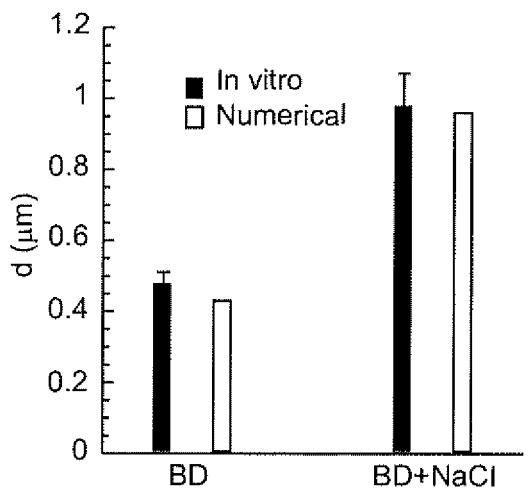
Figure 5D:
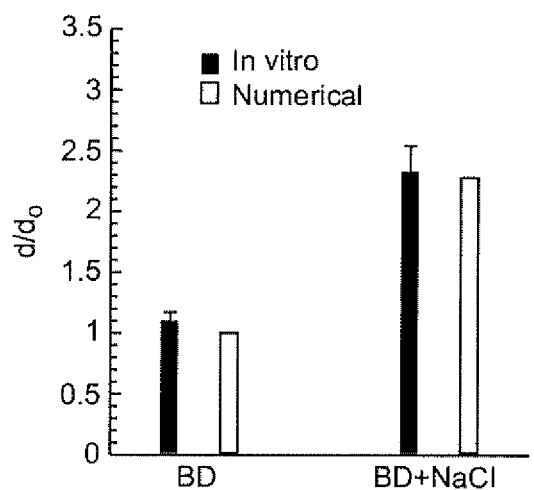

Experimental measurements were made in this study to determine the water activity coefficients of AS, CA, and PG. Activity coefficients for NaCl and MN were determined from the studies of Cinkotai (1971) and Ninni (2000), respectively. Budesonide is considered to be insoluble in water, and therefore has no hygroscopic effect during condensational growth. The experimentally determined activity coefficients of all soluble compounds considered are shown in FIG. 4 as a function of the soluble mass fraction of solute ($mf_s$) in water up to the saturation limit (Table 4). Two panels are used based on the presence of moderately soluble (AS, MN, and NaCl) and highly soluble (CA and PG) compounds. In order to represent the hygroscopic effect of molecular dissociation with a single coefficient, curve fits to the experimental data were based on Eq. (15) for a single component solution. The optimal value of i providing the best fit to the experimental data was calculated using a minimization routine. For compounds with high saturated mass fractions in water (CA and PG from Table 1), a limit of $mf_s<0.3$ was used for evaluating the i coefficients. This limit was used to ensure accuracy of the i-values for dilute droplets, which is needed to ensure accurate estimates of final droplet size. The resulting curve fits are shown in FIG. 4 and calculated i coefficient values are reported in Table 6. It is noted that the form of the activity coefficient correlation proposed by Hinds (1999) and translated to this study (Eq. 15), results in i coefficients that are slightly higher than with Raoult's law in the form reported by Finlay (2001). For example, the best fit for the NaCl data through $mf_s=0.3$ using Eq. (15) resulted in a coefficient of $i_{NaCl}=2.1$. In contrast, the Raoult's law form of the equation results in $i_{NaCl}=1.9$. As a result, care should be taken to ensure that the i coefficients determined in this study are used with the appropriate form of the activity coefficient expression, i.e., Eq. (15).

Model Validation

For the in vitro system, experimental measurements of initial and final aerosol sizes are provided in Table 4. The initial mass median aerodynamic diameter (MMAD) was measured at the inlet to the growth zone, as shown in FIG. 3. It was assumed that the aerosol at this location was composed of dry particles, resulting in the particle densities shown in the table. These density values were then used to calculate the initial geometric size of the particles ($d_{geo}$). Reported final geometric diameters are based on the measured MMADs and the assumption that the droplet density is $\rho_d \approx 1000$ kg/m$^3$ at the outlet of the growth tube. The aerosol growth ratio of final to initial size ($d/d_o$) was then based on the geometric diameters. Standard deviations of the experimental measurements are provided in parentheses based on a minimum of four experimental trials (Table 4). Experimental measurements of the flow field conditions indicate an average temperature and RH of 28° C. and 99% at the inlet to the growth zone (FIG. 3).

TABLE 4

Experimental results of growth for single and multiple component droplets.

| Particle components | $mf_{drug}$ | $n_{part}$ (part/cm$^3$) | $\rho_d$ (kg/m$^3$) | Initial MMAD (μm) | Initial $d_{geo}$ (μm) | Final $d_{geo}$ (μm)[b] | $d/d_o$[c] |
|---|---|---|---|---|---|---|---|
| AS | 1.0 | $4.8 \times 10^5$ | 1340. | 0.38 (0.01)[a] | 0.33 | 0.51 (0.04) | 1.55 (0.12) |
| AS + NaCl | 0.5 | $3.9 \times 10^5$ | 1650. | 0.49 (0.03) | 0.38 | 1.07 (0.09) | 2.82 (0.24) |
| BD | 1.0 | $6.5 \times 10^5$ | 1000. | 0.43 (0.02) | 0.43 | 0.48 (0.03) | 1.1 (0.7) |
| BD + NaCl | 0.5 | $4.7 \times 10^5$ | 1380. | 0.49 (0.05) | 0.42 | 0.98 (0.09) | 2.33 (0.21) |

[a]Standard deviations of the experiments are shown in parentheses based on a minimum of 4 trials.
[b]Final geometric diameters ($d_{geo}$) are assumed to be equal to the MMAD.
[c]Calculated based on the ratio of geometric diameters.

For numerical simulation of the in vitro system, the measured inlet conditions were applied in conjunction with $T_{wall}=24°$ C., $RH_{wall}=100\%$ and a particle residence time of 0.2 s. Comparisons of the in vitro experimental results and numerical predictions of the final geometric size and geometric diameter ratio ($d/d_o$) are shown in FIG. 5. Standard deviations of the in vitro measurements are provided as error bars on the experimental results. As shown in the figure, the numerical predictions are in good agreement with the experimental results and lie inside the standard deviation bars in most cases. Maximum relative errors between the numerical and experimental results are within approximately 10%. Based on this comparison, it appears that the numerical model can accurately predict the growth of both single and multiple component aerosols. The measured i coefficients also appear accurate. Moreover, the model accurately predicts the growth of soluble single drug particle and multiple component particles (AS and AS+NaCl) and combinations of soluble hygroscopic excipient and insoluble drug compounds (BD+NaCl).

Growth of Single Component Droplets

Figure 6A:
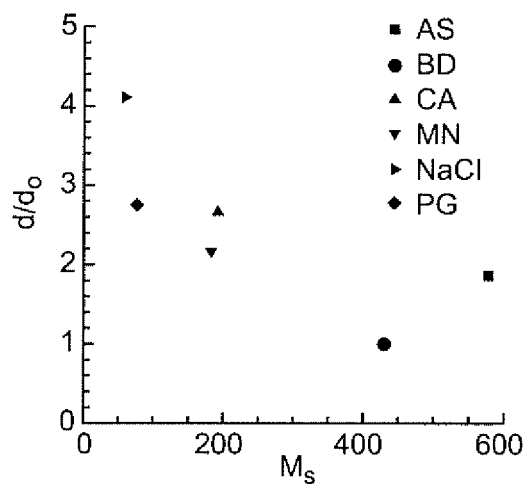
FIG. 6A-D. Geometric diameter growth ratio for single component aerosols (A) as a function of molecular weight, (B) as a function of the hygroscopic parameter, (C) for different initial solute mass fractions (mfs) in water, and (D) as a function of growth coefficient $GC_1$.
Figure 6B:
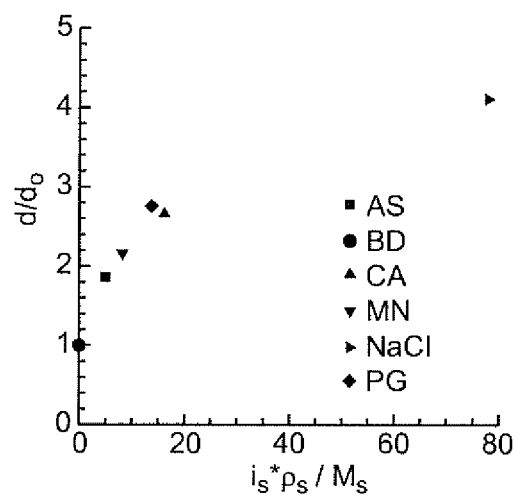
Figure 6C:
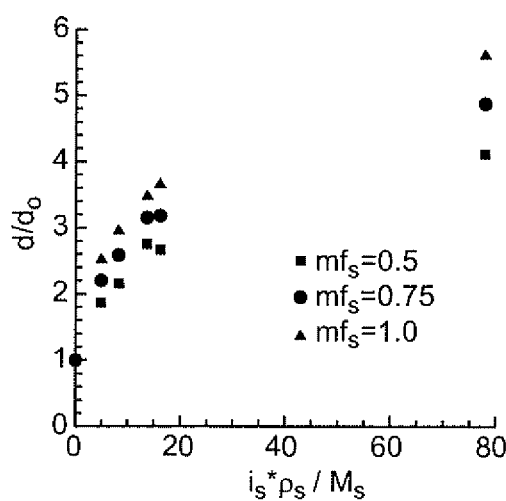
Figure 6D:
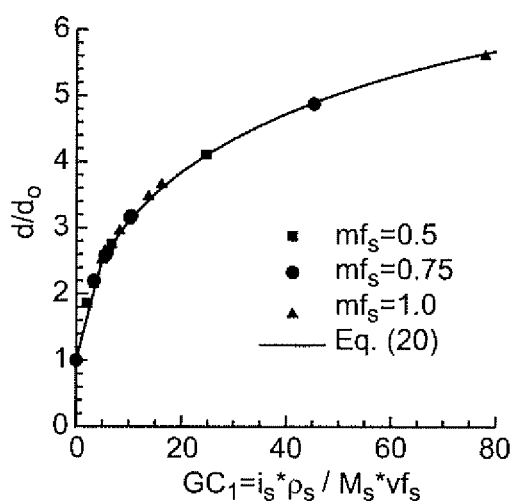

To better characterize the factors contributing to hygroscopic growth, droplets with a single dissolved species were first considered using the numerical model. As described previously, standard respiratory exposure conditions were assumed with wall conditions of $T_{wall}=37°$ C. and $RH_{wall}=99.5\%$ for a 2 s exposure period. The droplets had initial diameters of 900 nm, a soluble mass fraction of $mf_s=0.5$, and a number concentration of $3.9\times10^5$ part/cm$^3$. Hygroscopic properties influencing droplet growth affect the activity coefficient, as shown in Eq. (15), and include the experimentally determined i coefficients and the soluble mole fraction of the solute ($\chi_s$). Numerical results of the size growth ratio of droplet geometric diameter as a function of various growth factors are shown in FIG. 6. In FIG. 6A, the growth ratio demonstrates a clear inverse relationship with the molar mass of the solute ($M_s$) for both drugs and hygroscopic excipients. From Eq. (15), activity coefficients are lower (and growth is greater) for large values of $\chi_s$. Mole fractions of individual solutes in water are calculated as $$\chi_s = \frac{\frac{m_s}{M_s}}{\frac{m_s}{M_s} + \frac{m_w}{M_w}} \qquad (17)$$

where m and M represent the mass (kg) and molar mass (kg/kmol) of the solute (s) and water (w). Clearly, lower $M_s$ results in higher $\chi_s$, which reduces the activity coefficient and increases the particle size growth. However, the solute molar mass does not completely characterize the growth for the respiratory and particle conditions considered. FIG. 6B demonstrates that growth can be described for a single component particle and specific initial size by including both $i_s$ and $\rho_s$ in the growth coefficient. Based on Eq. (15), $i_s$ directly impacts the activity coefficient and $\rho_s$ influences the mass term in the mole fraction calculation (Eq. 17). The result is a "hygroscopic parameter" ($i_s\rho_s/M_s$) with units of kmol/m$^3$, which represents a molar density and describes the growth potential of a soluble compound. FIG. 6C illustrates that the initial mass fraction of the solute ($mf_s$) in the droplet influences size increase and causes the growth curves to separate. It is observed that increasing initial mass fractions of the solute from 0.5 to 1.0 increases the growth ratio by a factor of approximately 1.4. This effect of initial drug or excipient loading can be taken into account as a function of the initial solute volume fraction ($vf_s$). The resulting growth coefficient ($GC_1$) for a single component droplet is then $$GC_1 = \frac{i_s\rho_s}{M_s}vf_s \qquad (18)$$

and collapses the data for multiple initial mass fractions into a single well-defined growth curve (FIG. 6D). Here, the initial solute volume faction is calculated as $$vf_s = \frac{\frac{mf_s}{\rho_s}}{\frac{mf_s}{\rho_s} + \frac{mf_w}{\rho_w}} \qquad (19)$$

The use of $vf_s$ is preferred in defining $GC_1$ because the base growth coefficient has units of kmol/m$^3$. In contrast, use of $mf_s$ did not effectively reduce the data to a single curve. For insoluble compounds, like BD, $vf_s$ is taken to be zero. The correlation for single component droplet growth under the defined respiratory and particle conditions is then $$\frac{d}{d_o} = 1.0 - 0.0254(GC_1) + 0.75(GC_1)^{0.5} \qquad (20)$$

This expression is illustrated in FIG. 6D and produced a correlation coefficient of $R^2=0.998$, which indicates an excellent representation of the data. It is noted that this correlation is for a single component aerosol with a single initial diameter and number concentration. The influences of multiple components, particle properties, and aerosol characteristics are explored in the following section.

Growth of Multiple Component Particles

For the evaluation of multiple component aerosols, standard respiratory conditions are again assumed for a 2 s exposure period. Particle properties include initial diameters of 500, 900, and 1500 nm with an initial aerosol number concentration of $n_{part}=3.9\times10^5$ part/cm$^3$. Initial mass loadings of the drug and excipient are $mf_{drug}=0.5$ and $mf_{ex}=0.5$ resulting in no initial water in the particle. Predicted growth ratios for AS and BD combined with each excipient considered, and evaluated as pure drug aerosols, are displayed in FIG. 7. In FIG. 7A, growth ratios are plotted vs. the hygroscopic parameter evaluated for the excipient. At each growth coefficient value, the three initial particle diameters result in slightly different growth ratios due to two-way coupling effects and potential Kelvin effects (for the 500 nm aerosol). Furthermore, differences in hygroscopicity between AS and BD result in two different sets of curves with higher growth ratios for AS. To account for hygroscopic effects of both the excipient (ex) and drug, a growth coefficient ($GC_2$) for combination particles can be formulated as $$GC_2 = \frac{i_{ex}\rho_{ex}}{M_{ex}}vf_{ex} + \frac{i_{drug}\rho_{drug}}{M_{drug}}vf_{drug} \qquad (21)$$

Here of represents the initial soluble volume fraction of the excipient and drug. For insoluble compounds like BD, $vf_{drug}$ is set to zero. For all other compounds consider in this study, no limit on the volume fraction is required. As shown in FIG. 7, application of this coefficient collapses the data to an approximate single curve. The resulting correlation for combination particle growth over a range of initial sizes (500-1500 nm) and the specified respiratory and particle conditions is $$\frac{d}{d_o} = 1.0 + 0.60(GC_2)^{0.5} \qquad (22)$$

This correlation provides a good fit to the numerical data (FIG. 7B) and has a correlation coefficient of $R^2=0.983$. However, some variability is observed for the higher growth ratios as a result of the initial aerosol size.

Effect of Initial Excipient and Drug Loading

Figure 8:
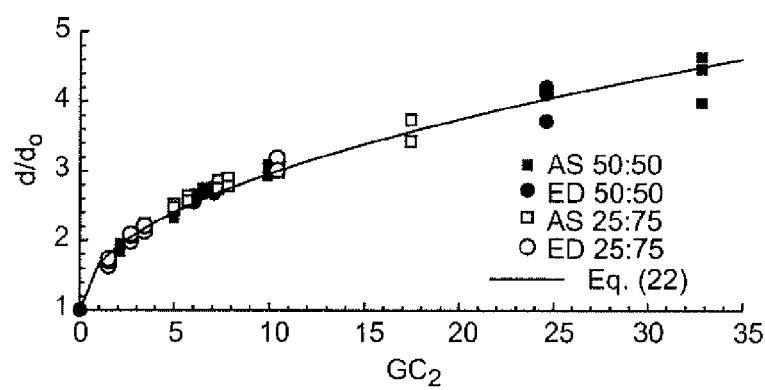
FIG. 8. Growth ratio as a function of $GC_2$ for initial mfex:mfdrug particle loadings of 50:50 and 25:75. Based on the use of the $GC_2$ parameter, the growth correlation represents size increase for multiple initial excipient and drug loadings.

The correlation developed above for combination particles (Eq. 22) was based on a single initial excipient and drug loading ratio of $mf_{ex}$:$mf_{drug}$=50:50. However, the $GC_2$ relation contains the initial volume fraction (vf), which should account for initial mass fraction loadings. To test if Eq. (22) works for multiple particle conditions, initial $mf_{ex}$:$mf_{drug}$ loading ratios of 50:50 and 25:75 were considered. Drug and excipient compounds included both model drugs and each hygroscopic excipient considered. Predicted growth ratios for these multiple initial loadings are shown in FIG. 8 compared with the developed combination particle correlation (Eq. 22). As shown in the figure, the correlation provides an excellent representation of multiple initial drug and excipient loadings. Furthermore, it is observed that reducing the excipient mass fraction from 0.5 to 0.25 produces a relatively small reduction in the final growth ratio.

Effect of Initial Particle Diameter

The combination particle correlation appears to provide a good estimate of growth for the conditions considered. However, for higher growth ratios ($d/d_o$>3 and $GC_2$>10), the initial aerosol size causes some variability in the data. This effect arises because of two-way coupling. As the aerosol grows larger, more water vapor is required to produce a size change and the amount of water vapor in the air limits the growth for a set exposure time. To address the effect of initial size, a correlation for unobstructed growth is first developed. The growth coefficient is then adjusted to account for both initial particle size and aerosol number concentration.

Unobstructed aerosol growth was considered for standard respiratory exposure conditions with no limit on the exposure time and without two-way coupling (i.e., approximately zero aerosol number concentration). The Kelvin effect was also neglected. As a result, all initial diameters produced the same growth ratio. The correlation representing this unobstructed growth is defined as $$\frac{d}{d_o} = 1.0 + 0.70(GC_2)^{0.5} \quad (23)$$

and illustrated in FIG. 9 ($R^2=0.999$).

Figure 9A:
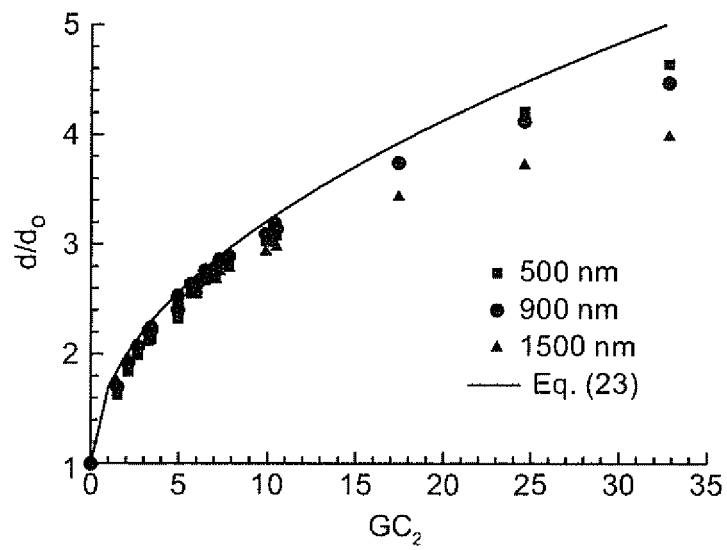
FIGS. 9A and B. Comparison of the correlation for unobstructed aerosol growth with growth data as a function of (A) $GC_2$ and (B) $GC_3$ for a range of initial aerosol sizes. Implementation of $GC_3$ with Eq. (23) fits the growth data very well for all initial aerosols sizes, drugs, and excipients considered.

To determine the effect of initial size on growth, standard respiratory conditions were considered for a 2 s exposure period. Particle properties included a $mf_{ex}$:$mf_{drug}$ loading ratio of 50:50, initial sizes of 500, 900, and 1500 nm, and an aerosol number concentration of $n_{part}$=3.9×10$^5$ part/cm$^3$. Numerical predictions of particle growth ratios for these conditions are shown in FIG. 9A compared with the unobstructed growth correlation. As expected, the realistic respiratory and particle conditions reduce growth ratios from the unobstructed case, and this reduction is greater for larger initial sizes and larger growth values.

Figure 9B:
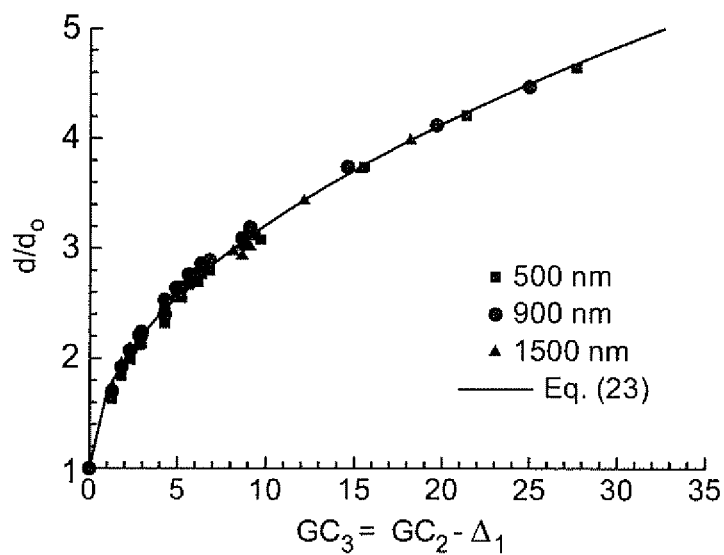

To fit the realistic numerical growth data to Eq. (23), effects of initial size were incorporated into the growth coefficient as $$GC_3 = GC_2 - \Delta_1 \quad (24)$$

where $GC_2$ is defined in Eq. (21). The $\Delta$ coefficient represents the decrease in the growth coefficient value arising from initial size effects. Best fits of the numerical data to Eq. (23) resulted in the following $\Delta$ values:

if $GC_2 \geq 10$ (25a)
$\Delta_1 = 0.0336 d_o (GC_2)^{1.62}$ if $GC_2 < 10$ (25b)
$\Delta_1 = \dfrac{GC_2}{0.125(GC_2) + 6.7}$ where the diameter term $d_o$ is the initial particle or droplet geometric diameter in micrometers (µm). The first $\Delta$ relation (Eq. 25a) indicates that both initial diameter and the amount of growth (represented by $GC_2$), influence the final particle size. For smaller $GC_2$ values (<10), Eq. (25b) indicates that the amount of growth is the primary factor in limiting the final size. The resulting growth coefficient fits the numerical data very well (FIG. 9B). Therefore, the combination of the unobstructed growth correlation (Eq. 23) with $GC_3$ (Eq. 24) can be used to accurately predict growth for multiple initial sizes, components, and loading ratios with an approximate number concentration of 3.9×10$^5$ part/cm$^3$.

Effect of Number Concentration

The previous results are based on a single aerosol number concentration of $n_{part}$=3.9×10$^5$ part/cm$^3$. This value is representative of the CAG delivering 10 mg/s of a drug solution. However, other deliver devices may produce different aerosol number concentrations when combined with the patent's inhalation flow rate. To consider the effects of aerosol number concentration, values of 3.9×10$^5$, 5.0×10$^6$, and 1.0×10$^7$ part/cm$^3$ were evaluated, which span a range of approximately two orders of magnitude. As before, standard respiratory exposure conditions were assumed for initial diameters of 500, 900, and 1500 nm and 50:50 excipient to drug initial mass ratio. Numerical predictions of growth for these different number concentrations are compared with Eq. (23) for growth coefficients $GC_2$ and $GC_3$ in FIGS. 10A and B, respectively. Aerosol number concentration is observed to reduce the growth ratio due to increasing two-way coupling effects. However, the $GC_3$ relation provides a reasonable approximation to growth through a concentration of 1.0×10$^7$ part/cm$^3$. The data for various number concentrations is fit very effectively using a new growth coefficient $$GC_4 = GC_2 - \Delta_2 \quad (26)$$

where for all values of $GC_2$, the effects of both initial particle size and number concentration can be approximated as $$\Delta_2 = 0.0443 d_o (GC_2)^{\sqrt{2}} \left(\frac{n_{part}}{1 \times 10^5}\right)^{0.154}$$

In this expression, the initial aerosol diameter $d_o$ is again entered in micrometers and the aerosol number concentration has units of particles/cm$^3$. FIG. 10C illustrates that the $GC_4$ relation combined with Eq. (23) fits the growth data very well across a range of drugs, excipients, initial sizes, loadings, and number concentrations.

Discussion

The numerical model developed in this study was found to accurately predict the size increase of single and multiple component pharmaceutical aerosols in comparison with in vitro experiments. For a fixed set of respiratory exposure conditions, the model was then used to explore the effects of hygroscopic characteristics, particle engineering parameters, and aerosol properties on particle size growth. Considering a single component aerosol, molar density of the solute ($i_s\rho_s/M_s$) was identified as a hygroscopic parameter that described the growth potential of the compound. Combination of this hygroscopic parameter with the volume fraction of the solute produced a growth coefficient ($GC_1$) that collapsed the single component growth data to a well defined curve. For combination particles, a sum of growth coefficients for the drug and excipient components ($GC_2$) was shown to correlate the growth data very well over a range of drugs, hygroscopic excipients, and initial particle sizes. The resulting correlation was also found to be valid for different initial drug to excipient mass loading ratios. For an initial $mf_{ex}$:$mf_{drug}$ ratio of 50:50, the final to initial diameter ratios ranged from approximately 2.3-4.6 for AS (a soluble hygroscopic drug) and from 2.1-4.2 for BD (an insoluble non-hygroscopic drug) over the spectrum of excipients that were considered. More detailed growth coefficients were then developed to better account for the effects of initial size and aerosol number concentration, which can both limit growth through two-way coupling. The growth coefficient presented in Eq. (26), i.e. $GC_4$, was shown to effectively predict aerosol size increase in the respiratory airways for a range of drugs, hygroscopic excipients, initial diameters, particle loading conditions, and aerosol number concentrations. It was observed that even at the maximum aerosol number concentration considered ($n_{part}=1\times10^7$ part/cm$^3$), Eq. (23) in combination with $GC_4$ predicted aerosol size increases up to 4.5 for the drugs and excipients considered in this study.

An interesting finding of this study was the correlation between the initial mole fraction (i.e., hygroscopic parameter) of the solute in the particle or droplet and the diameter growth ratio. The product of the hygroscopic parameter ($i_s\rho_s/M_s$) and volume fraction of the solute was then the basis for all droplet growth coefficients in this study. Based on these results, $i_s\rho_s/M_s$ values can be used to determine the hygroscopic growth characteristics of soluble drugs and excipients. Compounds with the greatest hygroscopic potential, and therefore good candidates for EEG delivery, have high i coefficients and low molecular weights ($M_s$). High density also increases the $i_s\rho_s/M_s$ parameter; however, high density may reduce the excipient volume fraction depending on the density of the drug. Table 3 provides values of $i_s\rho_s/M_s$ for all compounds considered in this study. The hygroscopic excipients are observed to all have $i_s\rho_s/M_s$ values at least double the value of AS, which makes them good candidates for EEG delivery. NaCl is by far the most hygroscopic compound considered, followed by CA and PG. The range of hygroscopic potential reported in Table 3 gives flexibility to drug formulators in order to engineer specific size increases and rates of increase to target deposition within different regions of the lungs. Furthermore, definition of the hygroscopic parameter provides valuable insight regarding the expected performance of other potential excipients and drugs that may be used for EEG delivery.

In this study, a range of correlations is provided for determining the hygroscopic growth of single and multi-component particles or droplets in the airways for typical respiratory conditions. The simpler correlations are most valid for a single initial size and number concentration where two-way coupled effects are limited. More advanced correlations are then required to account for the effects of the initial size, the initial concentration, and two-way coupling. For targeted aerosol drug delivery to the lungs, whole-lung 1-D models (Asgharian et al., 2001) or more detailed CFD models (Xi et al., 2008) of deposition can be used to determine the desired initial and final sizes of the aerosol. For example, negligible mouth-throat deposition typically occurs for 900 nm particles (Hindle and Longest 2010 U.S. patent application Ser. No. 12/866,869, published as PCT/US09/34360, the complete contents of which are herein incorporated by reference) and full lung retention can occur for 3.0 droplets (Stahlhofen et al., 1989) resulting in a final to initial diameter ratio of 3.3. The correlations provided in this study can then be used to engineer the particles to achieve the desired size increase and maximize the drug payload of the aerosol. For a quick calculation of expected size increase at typical EEG initial aerosols sizes (500-900 nm) and number concentrations ($n_{part}\approx 4\times 10^5$ part/cm$^3$), Eq. (22) in conjunction with $GC_2$ provides a simple relationship. Comparison between Eq. (22) and the unobstructed growth correlation Eq. (23) with $GC_2$ indicates that the former expression reduces the final diameter ratio by a maximum of 10% due to two-way coupling effects. For more precise calculations that effectively collapse the data to a single curve by accounting for both initial size and number concentration, Eq. (23) is recommended with the use of $GC_4$. Based on the implementation of three initial sizes (500-900 nm) and three aerosol number concentrations ($3.9\times10^5$-$1.0\times 10^7$ part/cm$^3$), $GC_4$ can be applied to both larger initial particle sizes and number concentrations than those considered in this study. Lower number concentrations are not expected to have a significant effect on growth and can therefore also be analyzed with the correlations developed in this study. However, caution should be exercised when applying the correlation to initial sizes less than 500 nm as Kelvin effects were included in the model but were not largely present over the size range considered. These correlations can also be used to describe the growth of conventional pharmaceutical aerosols composed of single and multiple components. Single component aerosols can be analyzed using either Eq. (20) or the more advanced relations with only one volume fraction retained. Moreover, aerosols with more than two components can be analyzed with the developed correlations by including additional terms in the $GC_2$ relations as follows $$GC_2 = \sum_{j=1}^{N} \frac{i_j \rho_j}{M_j} vf_j \qquad (28)$$

where the summation is performed over the total number of compounds (N). This expression can then be used in Eqs. (26) and (27) to define a $GC_4$ parameter for more than two compounds, which accounts for two-way coupling effects.

The utility of the developed correlations is illustrated by considering an example in which insulin is to be delivered using the EEG approach. Sample initial and final diameters are 900 nm and 3 μm for producing minimal mouth-throat deposition and nearly complete retention in the alveolar region. As a conservative estimate, insulin is assumed insoluble and NaCl is the hygroscopic excipient selected. It is also assumed that the delivery device produces an aerosol number concentration of $1\times10^6$ part/cm$^3$ ($1\times10^{12}$ part/m$^3$). To engineer the particles for optimal EEG delivery, the minimum mass loading of the hygroscopic excipient to produce the desired size change in the aerosol needs to be determined. Using the most detailed correlation developed, FIG. 10C or Eq. (23) indicate that the necessary value of $GC_4$ is 10.8. Solving Eq. (26) for a known $GC_4$ value then indicates an initial volume fraction of the hygroscopic excipient of 0.165, which translates to an initial excipient mass fraction of 0.30. Therefore, a relatively small amount of the hygroscopic excipient is required to produce the required growth to 3 μm for typical respiratory conditions with a non-hygroscopic drug and achieve full lung retention of the aerosol. Moreover, use of the developed correlation ensures that each particle delivers the maximum amount of drug and minimum amount of excipient possible for the prescribed aerosol growth.

In conclusion, the model and correlations developed in this study can be used to effectively describe particle properties that achieve a specified amount of size increase during EEG delivery under standard respiratory drug delivery conditions. These correlations can also be used to predict the size increase of conventional single and multicomponent aerosol in the respiratory airways. Considering EEG delivery, significant size increases were observed for a range of hygroscopic excipients combined with both hygroscopic and non-hygroscopic drugs. These size increases are expected to be sufficient to allow for minimal mouth-throat deposition and nearly full lung retention. The developed correlations can also be applied to screen the performance of other excipients and drugs not considered in the base set of sample compounds. Interesting, large diameter growth ratios were achieved at excipient mass loadings of 50% and below and at realistic aerosol number concentrations. It was illustrated that the developed correlations can be used to maximize drug content and minimize the necessary hygroscopic excipient of engineered particles to achieve a specific size increase. Future studies are needed to validation model predictions at longer residence times, consider variable lung conditions, determine aerosol size increase and deposition in more realistic airway models using CFD simulations and experiments, and assess model predictions compared with in vivo data.

Example 4

Aerosol Growth and Deposition during HFT

An enhanced condensational growth (ECG) approach has previously been proposed as a novel aerosol delivery strategy which combines the advantages of delivering submicrometer-sized aerosols with the pulmonary deposition properties of micrometer-sized particles (Hindle and Longest 2010 U.S. patent application Ser. No. 12/866,869, published as PCT/US09/34360, the complete contents of which are herein incorporated by reference). With ECG, a submicrometer aerosol is generated and delivered with saturated or supersaturated warm air. The system is designed so that the aerosol remains submicrometer-sized in the delivery tubing and in the extrathoracic airways. Mixing the drug aerosol and the humidified air streams, typically at the airway entrance, causes condensational growth to occur. The rate of growth can be controlled to allow the aerosol to remain small in the extrathoracic airways and thereby minimize deposition. Droplet growth to approximately 2 μm or greater in deeper regions of the respiratory tract then occurs to facilitate lung deposition and prevent exhalation.

With standard high-flow therapy (HFT), heated and humidified air is supplied continuously to the nasal airways through a cannula interface. The present invention provides methods and apparatuses in which this feature of HFT is used in conjunction with ECG to achieve improved delivery of aerosols to the lung. According to the invention, a submicrometer aerosol is delivered to one nostril at slightly subsaturated humidity conditions. Saturated air is delivered to the other nostril at a few degrees above body temperature. The nasal septum separates the subsaturated aerosol and saturated airstreams through the torturous nasal passages, resulting in minimal aerosol size change and deposition. The aerosol and humidified airstreams then mix in the nasopharynx region producing aerosol growth as the droplets continue downstream. Growth to approximately 2 μm is required for the aerosol to be retained in the lungs and not exhaled. To test this delivery concept, both in vitro experiments and Computational fluid dynamics (CFD) simulations were conducted for a standard nebulizer aerosol and the envisioned ECG dual stream nasal delivery concept, as described below.

A model of the nose, mouth, and throat (NMT) respiratory airways extending through midway the trachea was constructed. The model implemented adult geometries of the nasal cavity and mouth-throat regions. These individual elements have dimensions that are consistent with adult population means. The surface model was then used to construct an identical computational geometry (mesh) and hollow physical prototype. In both the in vitro experiments and CFD simulations, the aerosol was delivered to the right nostril at slightly subsaturated conditions with a flow rate of 10 L/min and air saturated with water vapor was supplied to the left nostril a few degrees above body temperature at a flow rate of 20 L/min. In the experimental setup, the submicrometer aerosol was formed using a small particle aerosol generator (SPAG) and the humidified air was supplied by a standard HFT delivery system (Vapotherm 2000i). Temperatures and relative humidities at the nostril inlets were experimentally measured and applied as boundary conditions in the CFD model. The walls of the geometry were wetted and maintained at a temperature of 37° C. The relative humidity (RH) field in the model for inlet aerosol conditions was 35° C. and 95% RH and inlet humidity conditions were 39° C. and 100% RH.

Results of the in vitro experiments and CFD simulations are presented in Table 5 in terms of final MMAD as the aerosol exits the NMT geometry and total deposition fraction in the model. As shown in the table, a control case was considered using a conventional ultrasonic nebulizer (Fisoneb, Fisons, UK), that produced a 4.67 μm aerosol. The ECG approach was considered in the other three cases for an aerosol with an initial MMAD of 900 nm and inlet conditions reported as aerosol temperature and the humidified saturated air temperature. Airway walls were not wetted for the control case to allow for aerosol evaporation and thereby minimize deposition, providing for the best possible performance. Considering the standard 4.67 μm aerosol (control case), significant deposition was observed within the nasal model (~73%), even though the aerosol was evaporating and exited with a size of 0.8 μm. The CFD model adequately predicted both the evaporated final size and total deposition fraction within the NMT geometry (Table 5).

TABLE 5

Growth and deposition for ECG delivery.

| Aerosol conditions | | Initial MMAD | Final MMAD (SD) | | Total Deposition fraction (%) (SD) | |
|---|---|---|---|---|---|---|
| | | | Experiment | CFD | Experiment | CFD |
| Standard ultrasonic nebulizer | | 4.67 (0.05) μm | 0.8 (0.3) μm | 0.73 μm | 72.6 (3.7) | 65.7 |
| ECG - | Aerosol - 21° C. Humidity - 39° C. | 900 (32.7) nm | 1.88 (0.09) μm | 2.25 μm | 14.8 (1.83) | 15.9 |
| ECG - | Aerosol - 35° C. Humidity - 39° C. | 900 (32.7) nm | — | 1.89 μm | — | 5.2 |
| ECG - | Aerosol - 35° C. Humidity - 42° C. | 900 (32.7) nm | — | 2.10 μm | — | 5.3 |

Experimental results show that for the ECG case with an aerosol temperature of 21° C. and a humidified air temperature of 39° C. (21:39° C.), aerosol deposition in the nasal model was low (~15%) and the aerosol exiting the model had increased in size due to condensational growth producing a MMAD near 2 μm. Additional simulations for cases of 35:39° C. and 35:42° C. showed that increasing the aerosol temperature (to improve patient comfort) resulted in even lower nasal deposition values (~5%) while maintaining an exit size of approximately 2 μm, which is suitable for pulmonary deposition (Table 5).

Trajectories of individual droplets for the ECG conditions of 35:39° C. and 35:42° C. were determined using CFD calculations. In both cases, deposition fractions in the nasal cavity are minimal (~1.5%) and increase slightly in the remainder of the geometry (~3.5%). As intended, the aerosol size is observed to remain less than 1 μm in the nasal cavity, resulting in negligible deposition. Continuous aerosol growth is then observed throughout the remainder of the model once the two streams are combined. The exit size for the 35:42° C. case is only slightly larger than with the 35:39° C. conditions (Table 5). However, all ECG conditions produce an approximately 2 μm aerosol that continues to grow as it enters the lungs.

Example 5

Generation of a Submicrometer Aerosol Using Low-Flow Drying Gases

Figure 11:
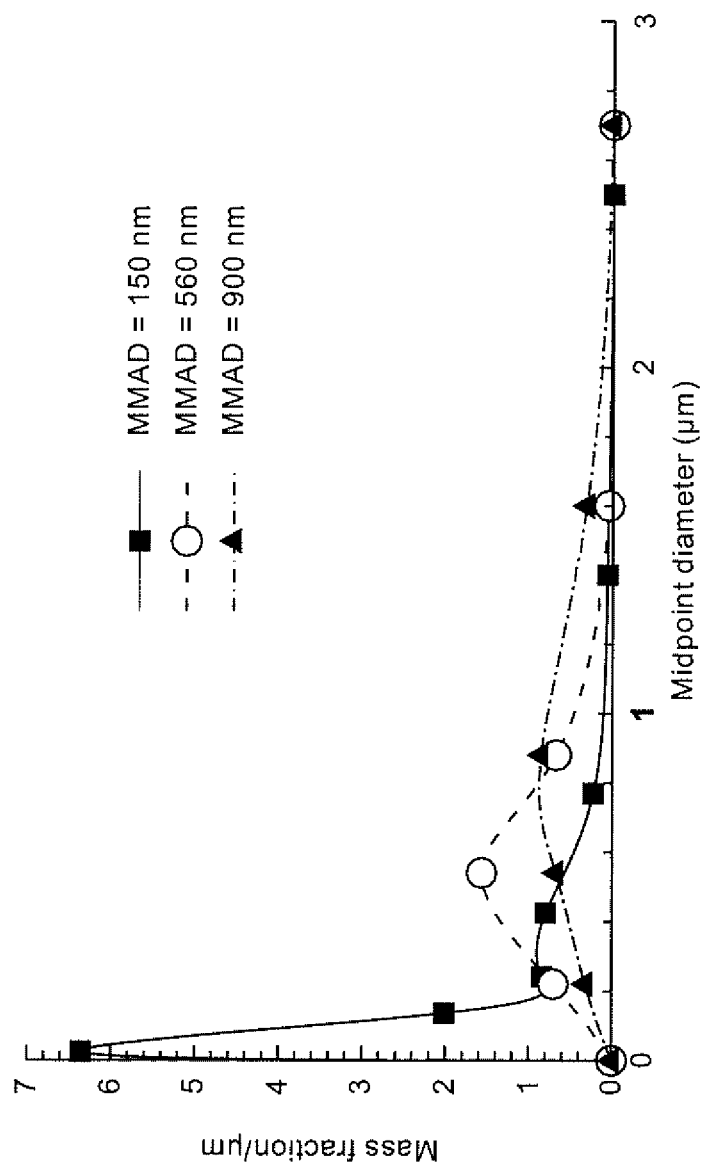
FIG. 11. Dried aerosol size distributions.

With LFT, a heated air source is not present for aerosol size reduction, as with HFT. However, medical gases used with LFT (oxygen and helium-oxygen) are typically dry. A study was conducted to evaluate if dry medical-grade gas could be used to produce a submicrometer aerosol from a commercially available nebulizer. A small particle aerosol generator (SPAG) was employed, which functions as a jet nebulizer with an additional relatively large and inefficient drying chamber. The SPAG was found to produce an aerosol with a diameter of approximately 5 μm, which could then be dried to submicrometer size. Specifically, albuterol sulfate solutions were nebulized and dried using a series of nebulizer airflow conditions to produce aerosols with initial mean MMADs (and standard deviations) of 150 (5.5) nm, 560 (11.4) nm, and 900 (32.7) nm (FIG. 11). The 560 nm aerosol was generated using a 0.1% albuterol sulfate in water solution with a nebulizer gas flow rate of 7.5 L/min and a drying gas flow rate of 3 L/min. The 900 nm aerosol was generated using a 0.5% albuterol sulfate in water solution with a nebulizer gas flow rate of 7 L/min and a drying gas flow rate of 3 L/min. As a result, it is concluded that dry gases in the range delivered during LFT (<6 L/min) can be used to produce submicrometer aerosols for respiratory drug delivery. Starting with a smaller MMAD aerosol will allow for further reductions in both dry gas requirements and resulting droplet size. Additional studies with the SPAG showed that combination particles consisting of a drug and hygroscopic excipient (budesonide and sodium chloride) could readily be produced in the size range of 430 nm.

Example 6

In Vitro Nasal Drug Delivery of Nano-Aerosols

Nano-sized aqueous-based drug aerosols were generated using a small particle aerosol generator (SPAG-6000, ICN Pharmaceuticals, Costa Mesa, Calif.), and were delivered through a nasal model geometry airway in the presence and absence of ECG conditions. Albuterol sulfate solutions were nebulized using a series of nebulizer airflow conditions to produce aerosols with initial mean (SD) measured size of 900 (32.7) nm. The aerosol was generated using a 0.5% albuterol sulfate in water solution nebulized with a nebulizer gas flow rate of 7 L/min and a drying gas flow rate of 3 L/min. Aerosols were generated into the nasal airway model for 30 seconds. The aerosol was delivered to the inlet of the nasal model corresponding to the left nostril. A modified compressed-air-driven humidifier system (Vapotherm 2000i, Stevensville, Md.) was employed to generate heated saturated and supersaturated ECG air conditions that were delivered to the other inlet of the nasal model corresponding to the right nostril at 20 L/min. In this example, drug aerosol and humidified air were delivered separately via individual nostrils passages. Saturated humidified air was delivered at a temperature of 39° C. corresponding to the ECG conditions. The total flow through the airway model was 30 L/min. The nasal model was preconditioned and maintained at a constant temperature and humidity (Espec Environmental Cabinet, Grand Rapids, Mich.) of 37° C. and 99% RH to ensure that the airway walls within the model were wetted and at equilibrium. Following passage through the model, aerosols were delivered to the Andersen Cascade Impactor (ACI, Graseby-Andersen Inc, Smyrna, Ga.) for particle sizing at a flow rate of 30 L/min. The exit of the model was connected directly to the impactor, which determines the particle size distribution of the aerosol after passage through the nasal airway model. The impactor was also maintained at a constant temperature and relative humidity of 37° C. and 99% RH (Espec Environmental Cabinet, Grand Rapids, Mich.). Temperature and relative humidity measurements were made using the HUMICAP Handheld Meter (HMP75, Vaisala, Helsinki, Finland).

For comparison, a commercially available handheld nebulizer was employed to deliver a larger aerosol to the nasal model. A Fisoneb ultrasonic nebulizer (Fisons Corp., Rochester, N.Y.) was used to generate a 4.7 µm large size aerosol using a 0.5% albuterol sulfate in water solution for 20 seconds. This aerosol was delivered to the inlet of the nasal model and cascade impactor as described above. Humidified air at a temperature of 25° C. was delivered to the other nostril inlet as control.

Following aerosol generation and deposition, the model was disassembled and wall washings were taken. Appropriate volumes of water were used to collect albuterol sulfate deposited on the walls of the model. The mean (SD) amount of drug deposited in each section of the model was determined by quantitative HPLC albuterol sulfate analysis of washing obtained from these surfaces. The deposition fraction results were expressed as a percentage of the total delivered dose of albuterol sulfate. The particle size distribution and mass of drug delivered to the impactor was also determined following aerosol generation. Washings were collected from the impaction plates to determine the drug deposition using appropriate volumes of water. The solutions were then assayed using the quantitative HPLC method. The mass of drug on each impaction plate was determined and used to calculate the final aerodynamic particle size distributions of the drug aerosols. Aerosol droplet size distributions were reported as albuterol sulfate mass distribution recovered from the impactor. The mass median aerodynamic diameter (MMAD) was defined as the particle size at the 50 percentile on a cumulative percent mass undersize distribution (D50) using linear interpolation. The mean (SD) total delivered dose was determined as the sum of the drug recovered from the nasal model and the cascade impactor.

Table 6 shows the individual and mean data for the % deposition of drug in the impactor and nasal model, together with the final aerosol particle size after passage through the nasal airway for the 900 nm aerosol administered under ECG conditions. The nano-aerosol was successfully able to penetrate the model nasal passages with only 14.8% of the delivered dose being deposited in the nasal model geometry. The remaining 85.2% was delivered to the impactor. This aerosol could be considered as the amount of aerosol that was capable of reaching the respiratory airways for local therapeutic action or systemic absorption. The 900 nm aerosol following exposure to ECG conditions when the two airstreams are mixed, was observed to have increased in size to 1.88 µm. This would be of sufficient size to be capable of depositing and being retained in the lung airways.

TABLE 6

Deposition and final particle size of 900 nm albuterol sulfate aerosol in the impactor and nasal model using ECG conditions.

|  | % Impactor | % Nasal model | MMAD (µm) |
|---|---|---|---|
| #3 | 84.99 | 15.01 | 1.95 |
| #5 | 83.48 | 16.52 | 1.92 |
| #6 | 87.13 | 12.87 | 1.78 |
| MEAN | 85.20 | 14.80 | 1.88 |
| SD | 1.83 | 1.83 | 0.09 |
| CV | 2.15 | 12.39 | 4.82 |

Table 7 shows the individual and mean data for the % deposition of drug in the impactor and nasal model, together with the final aerosol particle size after passage through the nasal airway for the 4.7 µm Fisoneb aerosol administered under control conditions (25° C. humidified air). In this example, the nasal model deposition was unacceptably high for pulmonary delivery, with 72.6% of the delivered dose being deposited in the nasal model and therefore not available for deposition in the lungs. Only 27% of the aerosol was successfully able to penetrate the nasal passageway revealing the current failings of this route of administration for commercially available devices with typical pharmaceutical aerosol particles sizes. The particle size distribution of the aerosol reaching the impactor was 0.8 µm, possibly indicating the presence of droplet evaporation during transport through the nasal model.

TABLE 7

Deposition and final particle size of 4.7 µm albuterol sulfate Fisoneb aerosol in the impactor and nasal model using control conditions.

|  | % Impactor | % Nasal model | MMAD (µm) |
|---|---|---|---|
| #17 | 32.16 | 67.84 | 1.03 |
| #18 | 28.40 | 71.60 | 0.88 |
| #19 | 25.21 | 74.79 | 0.77 |
| #20 | 23.95 | 76.05 | 0.39 |
| MEAN | 27.4 | 72.6 | 0.8 |
| SD | 3.7 | 3.7 | 0.3 |
| CV | 13.4 | 5.1 | 35.6 |

REFERENCES

Asgharian, B., Hofmann, W., and Bergmann, R. (2001) Particle deposition in a multiple-path model of the human lung. Aerosol Science and Technology, 34, 332-339.

Cinkotai, F. F. (1971) The behavior of sodium chloride particles in moist air. Journal of Aerosol Science, 2, 325-329.

Clift, R., Grace, J. R., and Weber, M. E. (1978) Bubbles, Drops, and Particles, Academic Press, New York.

Finlay, W. H. (2001) The Mechanics of Inhaled Pharmaceutical Aerosols, Academic Press, San Diego.

Green, D. W. (1997). "Perry's Chemical Engineers' Handbook." McGraw-Hill, New York.

Haefeli-Bleuer, B., and Weibel, E. R. (1988) Morphometry of the human pulmonary acinus. The Anatomical Record, 220, 401-411.

Hindle, M., Byron, P. R., Jashnani, R. N., Howell, T. M., and Cox, K. A. (1998) High efficiency fine particle generation using novel condensation technology. Proceedings of Respiratory Drug Delivery VI, R. N. Dalby, P. R. Byron, and S. J. Farr, eds., Interpharm Press, Inc., Buffalo Grove, Ill., 97-102.

Hindle, M., and Longest, P. W. (2010) Evaluation of enhanced condensational growth (ECG) for controlled respiratory drug delivery in a mouth-throat and upper tracheobronchial model. Pharmaceutical Research, 27, 1800-1811.

Hinds, W. C. (1999) Aerosol Technology: Properties, Behavior, and Measurement of Airborne Particles, John Wiley and Sons, New York.

Longest, P. W., Hindle, M., Das Choudhuri, S., and Byron, P. R. (2007) Numerical simulations of capillary aerosol generation: CFD model development and comparisons with experimental data. Aerosol Science and Technology, 41, 952-973.

Longest, P. W., and Kleinstreuer, C. (2005) Computational models for simulating multicomponent aerosol evaporation in the upper respiratory airways. Aerosol Science and Technology, 39, 124-138.

Ninni, L., Camargo, M. S., and Meirelles, A. J. A. (2000) Water activity in polyol systems. J. Chem. Eng. Data, 45, 654-660.

Stahlhofen, W., Rudolf, G., and James, A. C. (1989) Intercomparison of experimental regional aerosol deposition data. Journal of Aerosol Medicine, 2(3), 285-308.

Stein, S. W. and Myrdal, P. B. (2004) A theoretical and experimental analysis of formulation and device parameters affecting solution MDI size distributions, Journal of Pharmaceutical Sciences, 93 (8), 2158-2175.

Vargaftik, N. B. (1975) Tables on Thermophysical Properties of Liquids and Gases, Hemisphere, Washington, D.C.

Xi, J., Longest, P. W., and Martonen, T. B. (2008) Effects of the laryngeal jet on nano- and microparticle transport and deposition in an approximate model of the upper tracheobronchial airways. Journal of Applied Physiology, 104, 1761-1777.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of targeted delivery of an active agent to a region of the respiratory system of a patient in need thereof, comprising
    providing said active agent to said patient as individually aerosolized submicrometer particles or droplets which combine both
    i) said active agent; and
    ii) at least one hygroscopic excipient with a hygroscopic parameter $i_{ex}\rho_{ex}/M_{ex}$ of at least 7 kmol/m$^3$;
    wherein said active agent and said at least one hygroscopic excipient are present in said individually aerosolized submicrometer particles or droplets in amounts sufficient to cause a predetermined amount of hygroscopic growth of said individually aerosolized submicrometer particles or droplets during passage through airways having natural airway humidity levels of said patient
    wherein said individually aerosolized submicrometer particles or droplets have a growth coefficient $i_{ex}\rho_{ex}/M_{ex} \cdot vf_{ex} + i_{aa}\rho_{aa}/M_{aa} \cdot vf_{aa}$ of at least 2.8;
    where
        $i_{ex}$ is the molecular dissociation constant of said at least one hygroscopic excipient,
        $i_{aa}$ is the molecular dissociation constant of said active agent,
        $\rho_{ex}$ is the density of said at least one hygroscopic excipient,
        $\rho_{aa}$ is the density of said active agent,
        $M_{ex}$ is the molar mass of said at least one hygroscopic excipient,
        $M_{aa}$ is the molar mass of said active agent,
        $vf_{ex}$ is the solute volume fraction of said at least one hygroscopic excipient, and
        $vf_{aa}$ is the solute volume fraction of said active agent;
    wherein said individually aerosolized submicrometer particles or droplets are at least 250 nm in size;
    wherein submicrometer refers to size according to mass median aerodynamic diameter (MMAD);
    and wherein said predetermined amount of hygroscopic growth caused by said amounts of said active agent and said at least one hygroscopic excipient results in said individually aerosolized submicrometer particles or droplets growing to an aerodynamic diameter which reaches or surpasses 2 μm in size.

2. The method of claim 1, wherein said active agent is a medicament.

3. The method of claim 1, wherein said active agent is a peptide.

4. The method of claim 1, wherein said active agent is selected from the group consisting of agents for the treatment of asthma, agents for the treatment of respiratory disorders, anesthesia agents, nucleic acid molecules, anti-pain agents, anti-inflammation agents, anti-depressants, mood altering drugs, anti-viral agents, anti-bacterial agents, anti-fungal agents, anti-cancer agents, hormones, benzodiazepines and calcitonin.

5. The method of claim 1, wherein said predetermined amount of hygroscopic growth is sufficient to cause targeted deposition of said individually aerosolized submicrometer particles or droplets in a region of said respiratory system of said patient selected from the group consisting of: nasal cavity, trachea, lung, alveolar airways, tracheobronchial airways, upper tracheobronchial airways, lower tracheobronchial airways, and lower tracheobronchial-alveolar airways.

6. The method of claim 1, wherein said region of said respiratory system is the nasal cavity.

7. The method of claim 1, wherein said region of said respiratory system is the trachea.

8. The method of claim 1, wherein said region of said respiratory system is the lung.

9. The method of claim 1, wherein said region of said respiratory system is the alveolar airways.

10. The method of claim 1, wherein said region of said respiratory system is the tracheobronchial airways.

11. The method of claim 1, wherein said region of said respiratory system is the lower tracheobronchial-alveolar airways.

* * * * *